US011456071B2

(12) United States Patent
Viola et al.

(10) Patent No.: US 11,456,071 B2
(45) Date of Patent: *Sep. 27, 2022

(54) HEMOSTATIC PARAMETER DISPLAY

(71) Applicant: HemoSonics LLC, Charlottesville, VA (US)

(72) Inventors: Francesco Viola, Charlottesville, VA (US); William F. Walker, Charlottesville, VA (US); Gregory V. Browne, Victoria West (CA); Adam Looker, Victoria (CA); Bryan Roy, Cobble Hill (CA); Bjarne Hansen, Victoria (CA)

(73) Assignee: HemoSonics LLC, Charlottesville, VA (US)

(*) Notice: Subject to any disclaimer, the term of this patent is extended or adjusted under 35 U.S.C. 154(b) by 651 days.

This patent is subject to a terminal disclaimer.

(21) Appl. No.: 16/206,155

(22) Filed: Mar. 21, 2019

(65) Prior Publication Data
US 2019/0244692 A1 Aug. 8, 2019

Related U.S. Application Data

(63) Continuation of application No. 13/083,360, filed on Apr. 8, 2011, now Pat. No. 10,147,152.

(Continued)

(51) Int. Cl.
*G16H 40/60* (2018.01)
*G16H 15/00* (2018.01)
(Continued)

(52) U.S. Cl.
CPC .............. *G16H 40/60* (2018.01); *G16H 10/60* (2018.01); *G16H 15/00* (2018.01); *A61B 5/14* (2013.01);
(Continued)

(58) Field of Classification Search
CPC ........ A61B 5/14; A61B 5/1427; A61B 5/1405; A61B 5/150343; A61B 5/150755; G16H 40/60; G16H 15/00; G16H 10/60
See application file for complete search history.

(56) References Cited

U.S. PATENT DOCUMENTS

| 4,112,740 A | 9/1978 | Brandestini |
| 4,558,589 A | 12/1985 | Hemmes et al. |

(Continued)

FOREIGN PATENT DOCUMENTS

| AU | 2011237383 | 7/2014 |
| CN | 1816306 | 8/2006 |

(Continued)

OTHER PUBLICATIONS

Amukele, et al., "Comparison of plasma with whole blood prothrombin time and fibrinogen on the same instrument," American Journal of Clinical Pathology, vol. 133, No. 4, Apr. 2010, pp. 550-556.

(Continued)

*Primary Examiner* — Puya Agahi
(74) *Attorney, Agent, or Firm* — Meunier Carlin & Curfman LLC

(57) ABSTRACT

A system for displaying a plurality of hemostatic indexes is disclosed. The system includes a communication receiver configured to receive the hemostatic indexes and a graphical user interface (GUI) connected to the communication receiver and configured to simultaneously display the hemostatic indexes. The hemostatic indexes are derived from a plurality of independent measurements, such as the mechanical measurements determined using the sonorheometry systems and processes.

21 Claims, 15 Drawing Sheets

Related U.S. Application Data

(60) Provisional application No. 61/322,049, filed on Apr. 8, 2010.

(51) Int. Cl.
  *G16H 10/60* (2018.01)
  *A61B 5/15* (2006.01)
  *A61B 5/155* (2006.01)
  *A61B 5/145* (2006.01)

(52) U.S. Cl.
  CPC ............ *A61B 5/1405* (2013.01); *A61B 5/1427* (2013.01); *A61B 5/150343* (2013.01); *A61B 5/150755* (2013.01)

(56) References Cited

U.S. PATENT DOCUMENTS

| | | |
|---|---|---|
| 4,695,956 A | 9/1987 | Leveen et al. |
| 4,705,756 A | 11/1987 | Spillert et al. |
| 4,756,884 A | 7/1988 | Hillman et al. |
| 4,814,247 A | 3/1989 | Spillert et al. |
| 4,849,340 A | 7/1989 | Oberhardt |
| 4,852,577 A | 8/1989 | Smith et al. |
| 4,900,679 A | 2/1990 | Spillert et al. |
| 5,016,469 A | 5/1991 | Henderson |
| 5,036,286 A | 7/1991 | Holm-Kennedy |
| 5,056,357 A | 10/1991 | Dymling et al. |
| 5,091,304 A | 2/1992 | La Duca |
| 5,104,975 A | 4/1992 | McCormick et al. |
| 5,204,525 A | 4/1993 | Hillman et al. |
| 5,205,159 A | 4/1993 | Carr, Jr. |
| 5,234,839 A | 8/1993 | McCormick et al. |
| 5,273,517 A | 12/1993 | Barone et al. |
| 5,311,908 A | 5/1994 | Barone et al. |
| 5,331,964 A | 7/1994 | Trahey et al. |
| 5,473,536 A | 12/1995 | Wimmer |
| 5,487,387 A | 1/1996 | Trahey et al. |
| RE35,171 E | 3/1996 | McCormick et al. |
| 5,504,011 A | 4/1996 | Gavin et al. |
| 5,534,226 A | 7/1996 | Gavin et al. |
| 5,605,154 A | 2/1997 | Ries et al. |
| 5,606,971 A | 3/1997 | Sarvazyan et al. |
| 5,629,209 A | 5/1997 | Braun, Sr. et al. |
| 5,655,535 A | 8/1997 | Friemel et al. |
| 5,657,760 A | 8/1997 | Ying et al. |
| 5,673,699 A | 10/1997 | Trahey et al. |
| 5,744,898 A | 4/1998 | Smith et al. |
| 5,777,215 A | 7/1998 | Calatzis et al. |
| 5,800,781 A | 9/1998 | Gavin et al. |
| 5,810,731 A | 9/1998 | Sarvazyan et al. |
| 5,854,423 A | 12/1998 | Venegas |
| 5,888,826 A | 3/1999 | Ostgaard et al. |
| 5,899,861 A | 5/1999 | Friemel et al. |
| 5,921,928 A | 7/1999 | Greenleaf et al. |
| 5,952,560 A | 9/1999 | Collings et al. |
| 6,016,712 A | 1/2000 | Warden et al. |
| 6,039,691 A | 3/2000 | Walker et al. |
| 6,046,051 A | 4/2000 | Jina |
| 6,083,159 A | 7/2000 | Driscoll, Jr. et al. |
| 6,114,135 A | 9/2000 | Goldstein |
| 6,117,081 A | 9/2000 | Jago et al. |
| 6,135,957 A | 10/2000 | Cohen et al. |
| 6,213,950 B1 | 4/2001 | Cespedes et al. |
| 6,221,672 B1 | 4/2001 | Baugh et al. |
| RE37,171 E | 5/2001 | Busche et al. |
| 6,225,126 B1 | 5/2001 | Cohen et al. |
| 6,232,127 B1 | 5/2001 | Lane et al. |
| 6,264,609 B1 | 7/2001 | Herrington et al. |
| 6,270,459 B1 | 8/2001 | Konofagou et al. |
| 6,277,074 B1 | 8/2001 | Chaturvedi et al. |
| 6,283,917 B1 | 9/2001 | Jago et al. |
| 6,318,191 B1 | 11/2001 | Chen |
| 6,371,912 B1 | 4/2002 | Nightinggale et al. |
| 6,402,704 B1 | 6/2002 | McMorrow |
| 6,412,344 B1 | 7/2002 | Danicich et al. |
| 6,436,722 B1 | 8/2002 | Clark et al. |
| 6,451,610 B1 | 9/2002 | Gorman et al. |
| 6,454,714 B1 | 9/2002 | Ng et al. |
| 6,494,834 B2 | 12/2002 | Konofagou et al. |
| 6,508,768 B1 | 1/2003 | Hall et al. |
| 6,514,204 B2 | 2/2003 | Alam et al. |
| 6,535,835 B1 | 3/2003 | Rubin et al. |
| 6,537,819 B2 | 3/2003 | Cohen et al. |
| 6,573,104 B2 | 6/2003 | Carr, Jr. et al. |
| 6,613,286 B2 | 9/2003 | Braun et al. |
| 6,613,573 B1 | 9/2003 | Cohen |
| 6,632,678 B2 | 10/2003 | Aiken et al. |
| 6,685,646 B2 | 2/2004 | Cespedes et al. |
| 6,687,625 B2 | 2/2004 | Srinivasan et al. |
| 6,692,439 B1 | 2/2004 | Walker et al. |
| 6,716,168 B2 | 4/2004 | Nock et al. |
| 6,726,629 B1 | 4/2004 | Frinking et al. |
| 6,764,448 B2 | 7/2004 | Trahey et al. |
| 6,787,363 B2 | 9/2004 | Cohen et al. |
| 6,797,519 B2 | 9/2004 | Cohen et al. |
| 6,881,721 B2 | 4/2005 | Nakatomi et al. |
| 6,890,299 B2 | 5/2005 | Cohen et al. |
| 6,951,544 B2 | 10/2005 | Trahey et al. |
| 7,179,652 B2 | 2/2007 | Cohen et al. |
| 7,192,726 B1 | 3/2007 | Carr, Jr. et al. |
| 7,202,048 B2 | 4/2007 | Carr, Jr. |
| 7,207,939 B2 | 4/2007 | Husher |
| 7,247,488 B2 | 7/2007 | Ghai et al. |
| 7,261,861 B2 | 8/2007 | Kautzky |
| 7,374,538 B2 | 5/2008 | Nightingale et al. |
| 7,399,637 B2 | 7/2008 | Wright et al. |
| 7,422,905 B2 | 9/2008 | Clague et al. |
| 7,439,069 B2 | 10/2008 | Nippoldt et al. |
| 7,524,670 B2 | 4/2009 | Cohen et al. |
| D611,489 S | 3/2010 | Bell et al. |
| 7,674,616 B2 | 3/2010 | Farnam, III et al. |
| 7,732,213 B2 | 6/2010 | Cohen et al. |
| 7,892,188 B2 | 2/2011 | Walker et al. |
| 7,912,661 B2 | 3/2011 | Zeng |
| 7,972,271 B2 | 7/2011 | Johnson et al. |
| 8,058,023 B2 | 11/2011 | Gurbel |
| 8,110,392 B2 | 2/2012 | Battrell et al. |
| 8,372,343 B2 | 2/2013 | Goldstein |
| 8,548,759 B2 | 10/2013 | Walker et al. |
| 8,740,818 B2 | 6/2014 | Walker et al. |
| 9,272,280 B2 | 3/2016 | Viola et al. |
| 9,410,971 B2 | 8/2016 | Viola et al. |
| 9,915,671 B2 | 3/2018 | Schubert et al. |
| 9,977,039 B2 | 5/2018 | Viola et al. |
| 10,031,144 B2 | 7/2018 | Viola et al. |
| 10,161,944 B2 | 12/2018 | Viola et al. |
| 2002/0013530 A1 | 1/2002 | Cespedes et al. |
| 2002/0040187 A1 | 4/2002 | Alam et al. |
| 2002/0081741 A1 | 6/2002 | Braun et al. |
| 2003/0013958 A1 | 1/2003 | Govari et al. |
| 2003/0073244 A1 | 4/2003 | Cohen et al. |
| 2003/0105398 A1 | 6/2003 | Vitek |
| 2003/0113929 A1 | 6/2003 | Baugh et al. |
| 2003/0170883 A1 | 9/2003 | Martin et al. |
| 2003/0171676 A1 | 9/2003 | Trahey et al. |
| 2003/0199082 A1 | 10/2003 | Miller |
| 2003/0201878 A1 | 10/2003 | Bai et al. |
| 2003/0204141 A1 | 10/2003 | Nock et al. |
| 2004/0065143 A1 | 4/2004 | Husher |
| 2004/0068184 A1 | 4/2004 | Trahey et al. |
| 2004/0072357 A1 | 4/2004 | Stiene et al. |
| 2004/0076546 A1 | 4/2004 | Bissett |
| 2004/0088317 A1 | 5/2004 | Fabrick et al. |
| 2004/0167403 A1 | 8/2004 | Nightingale et al. |
| 2004/0203163 A1 | 10/2004 | Cohen et al. |
| 2004/0214337 A1 | 10/2004 | Kautzky |
| 2005/0004463 A1 | 1/2005 | Chen et al. |
| 2005/0015001 A1 | 1/2005 | Lec et al. |
| 2005/0053305 A1 | 3/2005 | Li et al. |
| 2005/0148899 A1 | 7/2005 | Walker et al. |
| 2005/0164373 A1 | 7/2005 | Oldham et al. |
| 2005/0215901 A1 | 9/2005 | Anderson et al. |
| 2005/0216987 P1 | 9/2005 | Murakami |

(56) References Cited

U.S. PATENT DOCUMENTS

| | | |
|---|---|---|
| 2005/0233460 A1 | 10/2005 | Clague et al. |
| 2007/0038095 A1 | 2/2007 | Greenleaf et al. |
| 2007/0059840 A1 | 3/2007 | Cohen et al. |
| 2007/0078631 A1 | 4/2007 | Ariyoshi et al. |
| 2007/0184508 A1 | 8/2007 | Cohen et al. |
| 2007/0259348 A1 | 11/2007 | Phadke et al. |
| 2007/0266778 A1 | 11/2007 | Corey et al. |
| 2007/0276236 A1 | 11/2007 | Jong |
| 2008/0038828 A1 | 2/2008 | Cohen et al. |
| 2008/0194967 A1 | 8/2008 | Sliwa et al. |
| 2008/0200343 A1 | 8/2008 | Clemens |
| 2008/0249408 A1 | 10/2008 | Palmeri et al. |
| 2008/0261261 A1 | 10/2008 | Grimes et al. |
| 2008/0297169 A1 | 12/2008 | Greenquist et al. |
| 2009/0112483 A1 | 4/2009 | Cohen |
| 2009/0130645 A1 | 5/2009 | Schubert et al. |
| 2009/0269837 A1 | 10/2009 | Shevkoplyas et al. |
| 2010/0154520 A1 | 6/2010 | Schubert |
| 2010/0190193 A1 | 7/2010 | Calatzis et al. |
| 2010/0274130 A1 | 10/2010 | Anand et al. |
| 2011/0034805 A1 | 2/2011 | Walker et al. |
| 2011/0151491 A1 | 6/2011 | Dennis et al. |
| 2011/0172661 A1 | 7/2011 | Designer et al. |
| 2011/0252352 A1 | 10/2011 | Viola et al. |
| 2012/0232803 A1 | 9/2012 | Viola et al. |
| 2012/0244392 A1 | 9/2012 | Kleiman |
| 2012/0252127 A1 | 10/2012 | Bansil et al. |
| 2012/0294767 A1 | 11/2012 | Viola et al. |
| 2013/0190584 A1 | 7/2013 | Walker et al. |

FOREIGN PATENT DOCUMENTS

| | | |
|---|---|---|
| CN | 101035479 | 9/2007 |
| CN | 103649751 | 3/2017 |
| EP | 1162457 | 12/2001 |
| EP | 1347058 | 9/2003 |
| EP | 1901065 | 3/2008 |
| EP | 2555704 | 2/2013 |
| EP | 2676143 | 12/2013 |
| WO | 2008093216 | 8/2008 |
| WO | 2009152094 | 12/2009 |
| WO | 2011035162 | 3/2011 |
| WO | 2011127436 | 10/2011 |
| WO | 2012159021 | 2/2012 |
| WO | 2013105987 | 10/2013 |

OTHER PUBLICATIONS

Anderson, "Multi-Dimensional Velocity Estimation with Ultrasound Using Spatial Quadrature," IEEE Transactions on Ultrasonics Ferroelectrics & Frequency Control, vol. 45, No. 3, 1998, pp. 852-861.

Anderson, "Preventing Deep Vein Thrombosis and Pulmonary Embolism," Center for Outcomes Research, U Mass Med Center, 1998, 23 pages.

Becker, R., "Cell-based models of coagulation: a paradigm in evolution," Journal of Thrombosis and Thrombolysis, vol. 20, No. 1, Aug. 2005, pp. 65-68.

Beer: Center for Reproductive Immunology & Genetics, "Thrombophilia: Inherited and Acquired," 6 pages, http://repro-med.net/papers/thromb.php. Mar. 30, 2005.

Bell, et al., "Thrombelastographic evaluation of coagulation in transurethral prostatectomy," British Journal of Urology, vol. 78, No. 5, 1996, pp. 737-741.

Bercoff et al., "In vivo breast tumor detection using transient elastography," Ultrasound in Medicine & Biology, vol. 29, No. 10, 2003, pp. 1387-1396.

Bercoff, et al., "Supersonic Shear Imaging: A New Technique for Soft Tissue Elasticity Mapping," IEEE Transactions on Ultrasonics Ferroelectrics & Frequency Control, vol. 51, No. 4, 2004, pp. 396-409.

Bilgen, et al., "Error analysis in acoustic elastography. II. Strain estimation and SNR analysis", Journal of the Acoustical Society of America, vol. 101, 1997, pp. 1147-1154.

Bohs, et al., "A Real Time System for Quantifying and Displaying Two-Dimensional Velocities using Ultrasound," Ultrasound in Medicine & Biology, vol. 19, No. 9, Jul. 1993, pp. 751-761.

Bombeli, et al., "Updates in perioperative coagulation: physiology and management of thromboembolism and haemorrhage," British Journal of Anaesthesia; vol. 93, No. 2, Aug. 2004, pp. 275-287.

Bonnefous, et al., "Time Domain Formulation of Pulse-Doppler Ultrasound and Blood Velocity Estimation by Cross Correlation," Ultrasonic Imaging 8, 1986, pp. 73-85.

Brock, et al., "Assessing Thrombin Generation at the Point of Care," Clinical Chemistry, vol. 55, No. 3, Mar. 2009, pp. 398-399.

Carr, M., "In vitro assessment of platelet function," Transfusion of Medicine Reviews, vol. 11, No. 2, Apr. 1997, pp. 106-115.

Carroll, et al., "Measurement of functional fibrinogen levels using the Thrombelastograph," Journal of Clinical Anesthesia, vol. 20, No. 3, May 2008, pp. 186-190.

Carter, G., "Coherence and time delay estimation," Proc IEEE, vol. 75, No. 2, 1987, pp. 236-255.

Chakroun et al., "The influence of fibrin polymerization and platelet-mediated contractile forces on citrated whole blood thromboelastography profile," Thrombosis and Haemostasis, vol. 95, No. 5, May 2006, pp. 822-828.

Chandler, et al., "Development of a rapid emergency hemorrhage panel," Tranfusion, vol. 50, No. 12, Dec. 2010, pp. 2547-2552.

Chandler, et al., "Estimating the rate of thrombin and fibrin generation in vivo during cardiopulmonary bypass," Blood, vol. 101, No. 11, Jun. 2003, pp. 4355-4362.

Chaturvedi, et al., "Testing the limitations of 2-D companding for strain imaging using phantoms," IEEE Transactions on Ultrasonics Ferroelectrics & Frequency Control, vol. 45, 1998, pp. 1022-1031.

Chavez, J., "A novel thrombelastograph tissue factor/kaolin assay of activated clotting times for monitoring heparin anticoagulation during cardiopulmonary bypass," Anesthesia and Analgesia; vol. 99, No. 5 Nov. 5, 2004, pp. 1290-1294.

Cohn et al., "An elasticity microscope. Part I: Methods," IEEE Transactions on Ultrasonics Ferroelectrics & Frequency Control, vol. 44, 1997, pp. 1304-1319.

Cohn et al., "An elasticity microscope. Part II: Experimental Results," IEEE Transactions on Ultrasonics Ferroelectrics & Frequency Control, vol. 44, 1997, pp. 1320-1331.

Craft, et al., "A novel modification of the Thrombelastograph assay, isolating platelet function, correlates with optical platelet aggregation," The Journal of Laboratory and Clinical Medicine, vol. 143, No. 5, May 2004, pp. 301-309.

Curry, et al., "Convention and near-patient tests of coagulation," British Journal of Anaesthesia, vol. 7, No. 2, Apr. 2007, pp. 45-50.

Dahlback, B., "Blood Coagulation," Lancet, vol. 355, No. 9215, May 2000, pp. 1627-1632.

Despotis, et al., "Monitoring of hemostasis in cardiac surgical patients: impact of point-of-care testing on blood loss and transfusion outcomes," Clinical Chemistry, vol. 43, No. 9, Sep. 1997, pp. 1684-1696.

Embree, et al., "Volumetric Blood Flow via Time-Domain Correlation: Experimental Verification," IEEE Transactions on Ultrasonics Ferroelectrics & Frequency Control, vol. 37, No. 2, May 1990, pp. 176-189.

Emelianov et al., "Ultrasound Elasticity Imaging of Deep Venous Thrombosis," Proc. IEEE Ultrasonics Symp., 2000, pp. 1791-1794.

Evans, et al., "Rheometry and associated techniques for blood coagulation studies," Medical Engineering and Physics, vol. 30, No. 6, Jul. 2008, pp. 671-679.

Fatemi et al., "C-Scan Imaging by Radiation Force Stimulated Acoustic Emission Method," Proc. IEEE Ultrasonics Symp., 1996, pp. 1459-1462.

Fatemi, et al., "Application of radiation force in noncontact measurement of the elastic parameters," Ultrasonic Imaging, vol. 21, No. 2, Apr. 1999 pp. 147-154.

Fatemi, et al., "Ultrasound-Stimulated Vibro-Acoustic Spectography," Science Magazine, vol. 280, No. 5360, 1998, pp. 82-85.

(56) References Cited

OTHER PUBLICATIONS

Ferraris, et al., "2011 Update to The Society of Thoracic Surgeons and the Society of Cardiovascular Anesthesiologists Blood Conservation Clinical Practice Guidelines," Annals of Thoracic Surgery, vol. 91, 2011, pp. 944-982.
Fertner, et al., "Comparison of Various Time Delay Estimation Methods by Comptuer Simulation," IEEE Transactions on Acoustics, Speech, and Signal Processing, vol. 34, No. 5, 1986, pp. 1329-1330.
Flax, et al., "Phase-Aberration Correction Using Signals from Point Reflectors and Diffuse Scatterers: Basic Principles," IEEE Transactions on Ultrasonics Ferroelectrics & Frequency Control, vol. 35, No. 6, Nov. 1988, pp. 758-767.
Freedman, et al., "A Meta-Analysis of Thromboembolic Prophylaxis Following Elective Total Hip Arthroplasty," Journal of Bone and Joint Surgery, vol. 82-A, 2000, pp. 929-938.
Gaetano, G. de, et al., "Effect of Platelets on Clot Structuration, a Thrombelastographic Study," Thrombosis Research, vol. 3, No. 4, pp. 425-435, 1973.
Ganter, et al., "Active, personalized, and balanced coagulation management saves lives in patients with massive bleeding," Anesthesiology, vol. 133, No. 5, Nov. 2010, pp. 1016-1018.
Gallippi, et al., "Adaptive clutter filtering via blind source," Ultrasonic Imaging, vol. 24, No. 4, 2002, pp. 193-214.
Gallippi, et al., "BSS-based filtering of physiological and ARFI-induced tissue and blood motion," Ultrasound in Medicine and Biology, vol. 29, No. 11, 2003, pp. 1583-1592.
Gallippi, et al., "Complex blind source separation for acoustic radiation force impulse imaging in the peripheral vasculature, in vivo," IEEE Ultrasonics Symposium, vol. 1, 2004, pp. 596-601.
Ganter, et al., "Coagulation monitoring: current techniques and clinical use of viscoelastic point-of-care coagulation devices," Anesthesia and Analgesia, vol. 106, No. 5, May 2008, pp. 1366-1375.
Gauss, et al., "Adaptive Imagining in the Thyroid Using Fundamental and Harmonic Echo Data," presented at IEEE Ultrasonics Symposium, 1999, pp. 1515-1519.
Gauss, et al., "Wavefront Estimation in the Human Breast," presented at SPIE Medical Imaging, vol. 4325, 2001, pp. 172-180.
Giunta, et al., "Estimation of Global Motion Parameters by Complex Linear Regression," IEEE Transactions on Image Processing, vol. 8, No. 11, 1999, pp. 1652-1657.
Glidden, Paul F., et al., "Thromboelastograph Assay for Measuring the Mechanical Strength of Fibrin Sealant Clots," Clinical and Applied Thombosis/Hemostasis, vol. 6, No. 4, Oct. 2000, pp. 226-233.
Gottumukkala, Vijaya N., et al., "Assessing Platelet and Fibrinogen Contribution to Clot Strength Using Modified Thromboelastography in Pregnant Women," Anesth Analg, vol. 89, 1999, pp. 1453-1455.
Greilich, Philip E., et al., "A Modified Thromboelastographic Method for Monitoring c7E3 Fab in Heparinized Patients," Anesth Analg, vol. 84, 1997, pp. 31-38.
Greilich, Philip E., et al., "Near-Site Monitoring of the Antiplatelet Drug Abciximad Using the Hemodyne Analyzer and Modified Thrombelastograph," Journal of Cardiothoracic and Vascular Anesthesis, vol. 13, No. 1, Feb. 1999, pp. 58-64.
Gurbel, et al., "Platelet function monitoring in patients with coronary artery disease," Journal of the American College of Cardiology, vol. 50, No. 19, Nov. 2007, pp. 1822-1834.
Hardisty R. M. et al, "Fibrinogen as a Co-factor in the Reaction of Platelets with Kaolin," May 7, 1966, Nature Publishing Group, Edition 210, vol. 644 (http://www.nature.com/nature/journal/v210/n5036/abs/210644a0.html).
Harris, et al., "Evaluation of recurrent thrombosis and hypercoagulability," American Family Physician, vol. 56, No. 6, Oct. 1997, pp. 1591-1596, pp. 1601-1602.
Hartley, et al., "Characteristics of Acoustic Streaming Created and Measured by Pulsed Doppler Ultrasound," IEEE Transactions on Ultrasonics, Ferroelectrics, and Frequency Control, vol. 44, No. 6, Nov. 1997, pp. 1278-1285.
Hartley, et al., "Doppler Measurement of Acoustic Streaming," IEEE Ultrasonics Symposium Proceedings, 1995, pp. 1537-1540.
Hett, et al., "Sonoclot Analysis," British Journal of Anaesthesia, vol. 75, No. 6, Dec. 1995, pp. 771-776.
Hirsh, et al., "How we diagnose and treat deep vein thrombosis," Blood, vol. 99, 2002, pp. 3102-3110.
Hirsh, et al., "Management of deep vein thrombosis and pulmonary embolism. A statement for healthcare professionals," Council on Thrombosis (in consultation with the Council on Cardiovascular Radiology), American Heart Association, vol. 93, 1996, 55 pages.
Hoffman, et al., "A cell-based model of hemostasis," Thrombosis and Haemostasis, vol. 85, No. 6, Jun. 2001, pp. 958-965.
Huang, et al., "Characterization of Blood Properties from Coagulating Blood of Different Hematocrits Using Ultrasonic Backscatter and Attenuation", Japanese Journal of Applied Physics, vol. 45, No. 9A, 2006, pp. 7191-7196.
Huang, et al., "Detection of blood coagulation and clot formation using quantitative ultrasonic parameters," Ultrasound in Medicine and Biology, vol. 31, No. 11, Nov. 2005, pp. 1567-1573.
Ickx, Brigitte, "Point-of-Care Monitoring of Haemostasis in the OR and the ICU," European Society of Anaesthesiologists. Jun. 5, 2004, pp. 79-83.
International Search Report and Written Opinion of the International Searching Authority, received in corresponding application PCT/US2010/049342, dated Nov. 16, 2010.
International Search Report and Written Opinion of the International Searching Authority, received in corresponding application PCT/US2011/031832, dated Dec. 15, 2011.
International Preliminary Report on Patentability and Written Opinion, dated Oct. 8, 2013, in connection with International Application No. PCT/US2012/025270.
International Search Report, dated Sep. 30, 2013, in connection with International Application No. PCT/US2012/025270.
International Preliminary Report on Patentability and Written Opinion, dated Aug. 27, 2013, in connection with International Application No. PCT/US2012/025278.
International Search Report, dated Aug. 20, 2013, in connection with International Application No. PCT/US2012/025278.
International Preliminary Report on Patentability and Written Opinion, dated Nov. 19, 2013, in connection with International Application No. PCT/US2012/038553.
International Search Report, dated Jan. 2, 2013, in connection with International Application No. PCT/US2012/038553.
International Preliminary Report on Patentability and Written Opinion, dated Oct. 9, 2012, in connection with International Application No. PCT/US2011/031832.
International Preliminary Report on Patentability and Written Opinion, dated Mar. 20, 2012, in connection with International Application No. PCT/US2010/049342.
Ivandic, et al., "Determination of clopidogrel resistance by whole blood platelet aggregometry and inhibitors of the P2Y12 receptor," Clinical Chemistry, vol. 52, No. 3, Mar. 2006, pp. 383-388.
Jacovitti, et al., "Discrete Time Techniques for Time Delay Estimation," IEEE Transactions on Signal Processing, vol. 41, No. 2, Feb. 1993, pp. 525-533.
Jensen, "A New Method for Estimation of Velocity Vectors," IEEE Transactions on Ultrasonics, Ferroelectrics and Frequency Control, vol. 45, No. 3, 1998, pp. 837-851.
Jensen, Estimation of Blood Velocities Using Ultrasound, 1996, pp. 195-225.
Jensen, et al., "Calculation of pressure fields from arbitrarily shaped, apodized, and excited ultrasound transducers," IEEE Transactions on Ultrasonics, Ferroelectrics, and Frequency Control, vol. 39, 1992, pp. 262-267.
Jolliffe, IT., "Principal Component Analysis," Springer Series in Statistics, 2nd edition, Springer, NY, 2002, pp. 1-8.
Kadi, et al., "On the performance of regression and step-initialized IIR Clutter Filters," IEEE Transactions on Ultrasonics, Ferroelectrics, and Frequency Control, vol. 42, 1995, pp. 827-837.
Kasai, et al., "Real-time Two-Dimensional Blood Flow Imaging Using an Autocorrelation Technique," IEEE Ultrasonics Symposium, vol. 32, No. 3, 1985, pp. 458-464.

(56) References Cited

OTHER PUBLICATIONS

Katori, et al., "The effects of platelet count on clot retraction and tissue plasminogen activator-induced fibrinolysis on thrombelastography," Anesthesia and Analgesia, vol. 100, No. 6, Jun. 2005, pp. 1781-1785.

Keresztes, et al., "The PFA-100: analysis and interpretation of a platelet function measurement," The Journal of Cardiovascular Nursing, vol. 20, No. 6, 2005, pp. 405-407.

Kettner, S.C., et al., "Use of abciximab-Modified Thrombelatography in Patients Undergoing Cardiac Surgery," Anesth Analg, vol. 89, 1999, pp. 580-584.

Khurana, Sandeep, et al., "Monitoring Platelet Glycoprotein IIb/IIa-fibrin Interaction with Tissue Factor-Activated Thromboelastography," J Lab Clin Med, vol. 130, No. 4, 1997, pp. 401-411.

Khurana, Sandeep, et al., "Thromboelastography Can Rapidly Bioassay Fibrinogen," Anesthesiology, vol. 85, No. 3A, Sep. 1996, p. A457.

Koepke, J., "Point-of-Care Coagulation Testing," Laboratory Medicine, vol. 31, No. 6, Jun. 2000, pp. 343-346.

Kruse, et al., "A new high-resolution color flow system using an eigendecomposition-based adaptive filter for clutter rejection," IEEE Transactions on Ultrasonics, Ferroelectrics, and Frequency Control, vol. 49, No. 10, 2002, pp. 1384-1399.

Ledoux, et al., "Reduction of the clutter component in Doppler ultrasound signals based on singular value decomposition: a simulation study," vol. 19, No. 1, 1997, pp. 1-18.

Lerner, et al., "Sono-elasticity: medical elasticity images derived from ultrasound signals in mechanically vibrated targets," Ultrasound in Medicine & Biology, vol. 16, 1998, pp. 317-327.

Libgot, R., et al., "High frequency ultrasound characterization of the blood clotting process: intra- and inter-individual variations," 2005 IEEE Ultrasonics Symposium, IEEE, vol. 4, 2005, pp. 2259-2262.

Loupas, et al., "An axial Velocity Estimator for Ultrasound Blood flow imaging, by means of a two-dimensional autocorrelation approach," IEEE Transactions on Ultrasonics, Ferroelectrics, and Frequency Control, vol. 42, No. 4, 1995, pp. 672-688.

Lubinski, et al., "Adaptive strain estimation using retrospective processing medical US elasticity imaging," IEEE Transactions on Ultrasonics Ferroelectrics & Frequency Control, vol. 46, 1999, pp. 97-107.

Mahla, et al., "Thromboelastography for monitoring prolonged hypercoagulability after major abdominal surgery," Anesthesia and Analgesia, vol. 92, No. 3, Mar. 2001, pp. 572-577.

Malinin, et al., "Validation of a VerifyNow-P2Y12 cartridge for monitoring platelet inhibition with clopidogrel," Methods and Findings in Experimental and Clinical Pharmacology, vol. 28, No. 5, Jun. 2006, pp. 315-322.

Mauldin, et al., "Robust Principal Component Analysis and Clustering Methods for Automated Classification of Tissue Response to ARFI Excitation," Ultrasound in Medicine & Biology, vol. 34, No. 2, 2008, pp. 309-325.

Mauldin, Jr., F.W., et al., "Adaptive Force Sonorheometry for Assessment of Whole Blood Coagulation," Clin Chim Acta, vol. 411, Issues 9-10, 2010, pp. 638-644.

Ng, et al., "A Comparative Evaluation of Several Algorithms for Phase Aberration Correction," IEEE Transactions on Ultrasonics Ferroelectrics & Frequency Control, vol. 41, No. 5, Sep. 1994, pp. 631-643.

McAleavey, et al., "Estimates of echo correlation and measurement bias in acoustic radiation force impulse imaging," IEEE Transactions on Ultrasonics Ferroelectrics & Frequency Control, vol. 50, 2003, pp. 631-641.

Nielson, er al., "Effects of coagulation factor deficiency on plasma coagulation kinetics determined via thrombelastography: critical roles of fibrinogen and factors II, VII, X and XII," Acta Anesthesiologica Scandanavia, vol. 49, No. 2, Feb. 2005, pp. 222-231.

Nightingale, et al., "Shear-Wave Generation Using Acoustic Radiation Force: In Vivo and EX Vivo Results," Ultrasound in Medicine & Biology, vol. 29, No. 12, 2003, pp. 1715-1723.

Nightingale, et al., "Acoustic Radiation Force Impulse Imaging: In Vivo Demonstration of Clinical Feasibility," Ultrasound in Medicine & Biology, vol. 28, 2002, pp. 227-235.

Nightingale, et al., "Acoustic remote palpation: initial in vivo results," presented at IEEE Ultrasonics Symposium, 2000, pp. 1553-1558.

Oberhardt, et al., "Dry reagent technology for rapid, convenient measurements of blood coagulation and fibrinolysis," Clinical Chemistry, vol. 37, No. 4, Apr. 1991, pp. 520-526.

O'Donnell, et al., "Role of the Thrombelastograph as an adjunctive test in thrombophilia screening," Blood Coagulation and Fibrinolysis, vol. 15, No. 3, Apr. 2004, pp. 207-211.

O'Donnell, et al., "Internal Displacement and Strain Imaging using Ultrasonic Speckle Tracking," IEEE Transactions on Ultrasonics, Ferroelectrics and Frequency Control, vol. 41, 1994, pp. 314-325.

Ophir, et al., "Elastography: A Quantitative Method for Imaging the Elasticity of Biological Tissues," Ultrasonic Imaging, vol. 13, No. 2, 1991, pp. 111-134.

Packham, M., "Role of platelets in thrombosis and hemostasis," Canadian Journal of Physiology and Pharmacology, vol. 72, No. 3, Mar. 1994, pp. 278-284.

Palmeri, et al., "Ultrasonic tracking of acoustic radiation force-induced displacements in homogeneous media," IEEE Transactions on Ultrasonics, Ferroelectrics, and Frequency Control, vol. 53, No. 7, 2006, pp. 1300-1313.

Parsons, et al., "Age Determiniation of Experimental Venous Thrombi by Ultrasonic Tissue Characterization," Journal of Vascular Surgery, vol. 17, 1993, 470-478.

Patil, et al., "3D prostate elastography: algorithm, simulations and experiments," Physics in Medicine & Biology, vol. 52, No. 12, 2007, pp. 3643-3663.

Perry, et al., "Point-of-care testing in haemostasis," British Journal of Haematology, vol. 150, No. 5, Sep. 2010, pp. 501-514.

Pivalizza, et al., "Perioperative thromboelastography and sonoclot analysis in morbidly obese patients," Canadian Journal of Anaesthesia, vol. 44, No. 9, Sep. 1997, pp. 942-945.

Rao, G., "Need for a point-of-care assay for monitoring antiplatelet and antithrombotic therapies," Stroke, vol. 40, No. 6, Jun. 2009, pp. 2271-2272.

Riou, et al., "Fast adaptive eigenvalue decomposition: a maximum likelihood approach," IEEE International Conference on Acoustics, Speech, and Signal Processing, vol. 5, 1997, pp. 3565-3568.

Rubin, et al., "Clinical application of sonographic elasticity imaging for aging of deep venous thrombosis: preliminary findings," Journal of Ultrasound in Medicine, vol. 22, 2003, pp. 443-448.

Sakharov, et al., "Acceleration of Fibrinolysis by High-Frequency Ultrasound: The Contribution of Acoustic Streaming and Temperature Rise," Thrombosis Research, vol. 100, No. 4, 2000, pp. 333-340.

Sarvazyan, et al., "Shear Wave Elasticity Imagining—A New Ultrasonic Technology of Medical Diagnostics," Ultrasound in Medicine and Biology, vol. 24, 1998, pp. 1419-1436.

Schmitt, C., et al., "Characterization of blood clot viscoelasticity by dynamic ultrasound elastography and modeling of the rheological behavior," Journal of Biomechanics, vol. 44, No. 4, 2011, pp. 622-629.

Shi, Quantitative Investigation of Acoustic Streaming in Blood, J. Acoust. Soc. Am. 111, Feb. 2002, pp. 1110-1121.

Shi, et al., "Color Doppler Detection of Acoustic Streaming in a Hematoma Model," Ultrasound in Medicine and Biology, vol. 27, No. 9, 2001, pp. 1255-1264.

Shi, et al., "Color Doppler imaging of acoustic streaming in blood and clot," IEEE Ultrasonics Symposium, vol. 2, 1999, pp. 1315-1318.

Shi, et al., "Experimental Investigation and Finite Element Simulation of Streaming in Blood in Cylindrical Models," IEEE Ultrasonics Symposium, vol. 2, 2000, pp. 1509-1512.

Shih, C-C, et al., "In Vitro Assessments of Viscoelastic Properties of Fibrin Clot by Using Acoustic Radiation Force on a Solid Sphere," International Ultrasonics Symposium Proceedings, IEEE, 2010, pp. 479-482.

(56) References Cited

OTHER PUBLICATIONS

Shung, et al., "Ultrasonic characterization of blood during coagulation," Journal of Clinical Ultrasound, vol. 12, No. 3, 1984, pp. 147-153.
Skovoroda, et al., "Tissue elasticity reconstruction based on ultrasonic displacement and strain images," IEEE Transactions on Ultrasonics, Ferroelectrics, and Frequency Control, vol. 42, No. 4, 1995, pp. 747-765.
Spiel, A. O. et al.,"Validation of rotation thrombelastography in a model of systemic activation of fibrinolysis and coagulation in humans", Journal of Thrombosis and Haemostasis, 2006; 4: 411-416.
Srinivasan, et al., "Elastographic imaging using staggered strain estimates," Ultrasonic Imaging, vol. 24, 2002, pp. 229-245.
Strobach, P., "Low-rank adaptive filters," IEEE Trans Signal Process, vol. 44, No. 12, 1996, pp. 2932-2947.
Sugimoto, et al., "Tissue Hardness Measurement Using the Radiation Force of Focused Ultrasound," Proc. IEEE Ultrason. Symp., 1990, pp. 1377-1380.
Sumino, et al., "Measurements of ultrasonic pulse arrival time differences produced by abdominal wall specimens," Journal of the Acoustical Society of America, vol. 90, No. 6, 1991, pp. 2924-2930.
Thuerlemann, et al., "Monitoring thrombin generation by electrochemistry: development of an amperometric biosensor screening test for plasma and whole blood," Clinical Chemistry, vol. 55, No. 3, Mar. 2009, pp. 505-512.
Toner, et al., "Blood-on-a-chip," Annual Review of Biomedical Engineering, vol. 7, 2005, pp. 77-103.
Torr, "The Acoustic Radiation Force," Am. J. Phys., vol. 52, 1984, pp. 402-408.
Trahey, et al., "Synthetic receive aperture imaging with correction for motion and for tissue inhomogeneities. II. Effects of and correction for motion," IEEE Transactions on Ultrasonics, Ferroelectrics, and Frequency Control, vol. 39, No. 4, 1992, pp. 496-501.
Traverso C, Arcelus JI, Gomez E, Luna D, Lopez-Cantarero M, Garcia JM. "Prospective assessment of the risk of deep vein thrombosis in elective abdominal surgery. Predictive role of [Thrombelastograph® analysis]." Thromb Haemorrh Disorders. 1993;71:9-15.
Vig, et al., "Thromboelastography: a reliable test?" Blood Coagulation and Fibrinolysis, vol. 12, No. 7, Oct. 2001, 555-561.
Viola, et al., "A Comparison between spline-based and phase-domain time-delay estimators," IEEE Transactions on Ultrasonics, Ferroelectrics, and Frequency Control, vol. 53, No. 3, 2006, pp. 515-517.
Viola, Francesco, et al., "A Novel Ultrasound-Based Method to Evaluate Hemostatic Function of Whole Blood," Clin Chim Acta, vol. 411, Nos. 1-2, 2010, pp. 106-113.
Viola, et al., "A comparison of the performance of time-delay estimators in medical ultrasound," IEEE Transactions on Ultrasonics Ferroelectrics & Frequency Control., vol. 50, 2003, pp. 392-401.
Viola, et al., "A Spline Based Algorithm for Continuous Time Delay Estimation Using Sampled Data," IEEE Transactions on Ultrasonics Ferroelectrics & Frequency Control, in press, 2005, pp. 80-93.
Viola, et al., "Analysis of Clot Formation with Acoustic Radiation Force," SPIE Proceedings, vol. 4689, 2002, pp. 235-242 and pp. 1-2.
Viola, et al., "Comparison of Time Delay Estimators in Medical Ultrasound," IEEE Ultrasonics Symposium, vol. 2, 2001, pp. 1485-1488.
Viola, et al., "Efficient and Accurate Spline-Based Time Delay Estimation," IEEE Ultrasonics Symposium, vol. 2, 2004, pp. 870-873.
Viola, et al., "Imaging Viscoelastic Properties of the Vitreous," Ultrasonics Symposium, vol. 2, 2001, pp. 1623-1626.
Viola, et al., "Radiation Force Imaging of Viscoelastic Properties with Reduce Artifacts," IEEE Transactions on Ultrasonics, Ferroelectrics, and Frequency Control, vol. 50, No. 6, 2003, pp. 736-742.
Viola, et al., "Sonorheometry: A new Method for Assessing coagulation potential," IEEE Ultrasonics Symposium, vol. 1, 2007, pp. 1001-1004.
Viola, et al., "Sonorheometry: A Noncontact Method for the Dynamic Assessment of Thrombosis," The Annals of Biomedical Engineering, vol. 32, 2004, pp. 696-705.
Viola, et al., "Ultrasound echo decorrelation due to acoustic radiation force," IEEE Ultrasonics Symposium Proceedings, vol. 2, 2002, pp. 1903-1906.
Voleišis, A., et al., "Ultrasonic method for the whole blood coagulation analysis," Ultrasonics, vol. 40, May 2002, pp. 101-107.
Walker, et al., "A Fundamental Limit on Delay Estimation Using Partially Correlated Speckle Signals," IEEE Transactions on Ultrasonics, Ferroelectrics and Frequency Control, vol. 42, 1995, pp. 301-308.
Walker, et al., "A Fundamental Limit on the Accuracy of Speckle Signal Alignment," IEEE Ultrasonics Symposium Proceedings, vol. 3, 1994, pp. 1787-1791.
Walker, et al., "A Method of Imagining Viscoelastic Parameters with Acoustic Radiation Force," Physics in Medicine and Biology, vol. 45, No. 6, 2000, pp. 1437-1447.
Walker, et al., "Application of Acoustic Radiation Force in Ophthalmic Ultrasound," Proc. IEEE Ultrason. Symp., vol. 2, 1997, pp. 1291-1295.
Walker, et al., "Real-Time Imaging of Tissue Vibration Using a Two-Dimensional Speckle Tracking System," IEEE Ultrason. Symp., 1993, pp. 873-877.
Walker, et al., "The Significance of Correlation in Ultrasound Signal Processing," SPIE Proceedings, vol. 4325, 2001, pp. 159-171.
Westbrook, et al., "Protocol based on thromboelastograph (TEG) out-performs physician preference using laboratory coagulation tests to guide blood replacement during and after cardiac surgery: a pilot study," Heart, Lung, and Circulation, vol. 18, No. 4, Aug. 2009, pp. 277-288.
Whitten, et al., "Thromboelastography: past, present, and future," Anesthesiology, vol. 92, No. 5, May 2000, pp. 1223-1225.
Yu, et al., "Single-Ensemble-Based Eigen-Processing Methods For Color Flow Imaging," IEEE Transactions on Ultrasonics, Ferroelectrics, and Frequency Controls, vol. 55, No. 3, 2008, pp. 573-587.
Azar et al., "Abciximab in Primary Coronary Angioplasty for Acute Myocardial Infarction Improves Short- and Medium-Term Outcomes", J. Am. Coll. Cardiol., Dec. 1998; 32(7):1996-2002. PubMed P.M.I.D.: 9857884.
Born, G.V., "Aggregation of Blood Platelets by Adenosine Diphosphate and its Reversal". Nature, Jun. 9, 1962; 194:927-9. PubMed P.M.I.D.: 13871375.
Callé et al., "Evaluation of the Sensitivity of an in vitro High Frequency Ultrasound Device to Monitor the Coagulation Process: Study of the Effects of Heparin Treatment in a Murine Model". Ultrasound Med. Biol., Feb. 2010; 36(2):295-305. PubMed P.M.I.D.: 20045589.
Coiffic et al., "Inhibition of Platelet Aggregation by Abciximab but not by Aspirin can be Detected by a New Point-of-Care Test, the Hemostatus". Thromb. Res., Jul. 15, 1999, 95(2):83-91. PubMed P.M.I.D.: 10418797.
Communication pursuant to Article 94(3) EPC dated Nov. 18, 2019, for European Application No. 12865373.0, 7 pages.
Communication pursuant to Rule 114(2) EPC issued in European Patent Application No. 12865280.7, dated Dec. 13, 2016, 5 pages.
Communication pursuant to Rule 94(3)) EPC issued in European Patent Application No. 12865280.7, dated Jul. 3, 2017, 3 pages.
Communication pursuant to Article 94(3) EPC issued in European Patent Application No. 12865280.7, dated Apr. 3, 2018.
Extended Search Report issued in European Application No. 12865280, dated Oct. 24, 2016, 5 pages.
Examination Report issued in European Application No. 12865280.7, dated Mar. 7, 2017, 3 pages.
Communication pursuant to Article 94(3) EPC issued in European Patent Application No. 12865280.7, dated Oct. 8, 2018.
Communication pursuant to Article 94(3) EPC issued in European Patent Application No. 12865280.7, dated Mar. 18, 2019.

(56) References Cited

OTHER PUBLICATIONS

Summons to attend oral proceeding pursuant to Rule 115(1) EPC European Patent Application No. 12865280.7, dated Dec. 5, 2019.
Declaration of U.S. Pat. No. 9,272,280, 67 pages.
Declaration of U.S. Pat. No. 9,410,971,124 pages.
Delhaye et al., Temperature corrected thromboelastometry in hypothermic trauma patients: 6AP24. European Journal of Anaesthesiology, May/Jun. 2008, 25:84.
Dorn-Beineke et al., "Evaluation of the Automated Coagulation Analyzer Sysmex CA-7000". Thromb. Res., 2005; 116(2):171-9. PubMed P.M.I.D.:15907533.
Douning et al., "Temperature Corrected Thrombelastography in Hypothermic Patients". Anesthesia & Analgesia, Oct. 1995; 81(3):608-11.
Eikelboom et al., "Monitoring Unfractionated Heparin with the aPTT: Time for a Fresh Look". Thromb. Haemost. Nov. 2006; 96(5):547-52. Review. PubMed P.M.I.D.: 17080209.
Extended European Search Report issued in European Patent Application No. 11766842.6, dated Oct. 21, 2015, 10 pages.
Communication pursuant to Article 94(3) EPC in pending European Application No. 11766842.6 (EP2555704), dated Jun. 14, 2017, pp. 1-6.
Summons to attend oral proceedings to Rule 115(1) EPC issued in European Patent Application No. 11766842.6, dated Apr. 18, 2018.
Flanders et al., "Evaluation and Performance Characteristics of the STA-R Coagulation Analyzer". Clin Chem., Sep. 2002; 48(9):1622-4. PubMed P.M.I.D.: 12194955.
Ganter et al., "Kaolin-Based Activated Coagulation Time Measured by Sonoclot in Patients Undergoing Cardiopulmonary Bypass." J. Cardiothorac. Vasc. Anesth, Aug. 2007; 21(4):524-8. PubMed P.M.I.D.: 17678778.
Gorlinger et al., "Recommendations for using the ROTEM® in the management of perioperative bleeding in Cardiac Surgery" Recommendations from the ROTEM® Expert Meeting Working Group, Munich 2007, 10 pages.
Gosselin et al., "Monitoring Oral Anticoagulant Therapy with Point-of-Care Devices: Correlations and Caveats". Clin. Chem., Sep. 1997; 43(9):1785-6. PubMed P.M.I.D.: 9299978.
Harrison, P. Platelet Function Analysis. Blood Rev. Mar. 2005; 19(2):111-23. Review. PubMed P.M.I.D.: 15603914.
Hirsh et al., "Oral anticoagulants. Mechanism of Action, Clinical Effectiveness, and Optimal Therapeutic Range". Chest. Oct. 1992; 102(4 Suppl.):312S-326S. Review. PubMed P.M.I.D.: 1345417.
Jobes et al., "Increased Accuracy and Precision of Heparin and Protamine Dosing Reduces Blood Loss and Transfusion in Patients Undergoing Primary Cardiac Operations". J. Thorac. Cardiovasc. Surg. Jul. 1995; 110(1):36-45. PubMed P.M.I.D.: 7609566.
Kereiakes et al., "Time Course, Magnitude, and Consistency of Platelet Inhibition by Abciximab, Tirofiban, or Eptifibatide in Patients with Unstable Angina Pectoris Undergoing Percutaneous Coronary Intervention". Am. J. Cardiol., Aug. 15, 1999; 84(4):391-5. PubMed P.M.I.D.: 10468074.
Koster et al., "Evaluation of Post-Cardiopulmonary Bypass Coagulation Disorders by Differential Diagnosis with a Multichannel Modified Thromboelastogram: A Pilot Investigation". J. Extra. Corpor. Technol., Sep. 2001; 33(3):153-8. PubMed P.M.I.D.: 11680728.
Lang et al., "Multi-center investigation on reference ranges from ROTEM thromboelasatometry", Blood coagul. Fibrinol 16:4, 2005, pp. 301-310.
Lang, T., et al., "Different effects of abciximab and cytochalasin D on clot strength in thrombelastography," Journal of Thrombosis and Haemostasis, 2: 147-153 (2004), PubMed P.M.I.D.: 14717978.
Li et al., "The Xylum Clot Signature Analyzer: A Dynamic Flow System that Simulates Vascular Injury". Thromb. Res., Dec. 15, 1998; 92(6 Suppl. 2):S67-77. PubMed P.M.I.D.: 9886913.
Machado et al., "Evaluation of an Ultrasonic Method Applied to the Measurement of Blood Coagulation Time". Physiol. Meas., May 1997; 18(2):129-43. PubMed P.M.I.D.: 9183807.
Motovska et al., "Benefits and Risks of Clopidogrel Use in Patients with Coronary Artery Disease: Evidence from Randomized Studies and Registries". Clin. Ther., 2008; 30 Pt. 2:2191-202. J. Clinthera., 2008.12.001. Review. PubMed P.M.I.D.: 19281914.
Mueller et al., "Utility of the PFA-100 Instrument and the Novel Multiplate Analyzer for the Assessment of Aspirin and Clopidogrel Effects on Platelet Function in Patients with Cardiovascular Disease". Clin. Appl. Thromb. Hemost., Dec. 2009; 15(6):652-9. PubMed P.M.I.D.: 18805846.
Nam et al., "Evaluation of the Roche CoaguChek XS Handheld Coagulation Analyzer in a Cardiac Outpatient Clinic". Ann. Clin. Lab. Sci., 2008 Winter; 38(1):37-40. PubMed P.M.I.D.: 18316780.
Pallister CJ, Watson MS (2010). Haematology. Scion Publishing. pp. 336-347. ISBN 1-904842-39-9.
Patent Examination Report No. 1 for Australian Application No. 2017201112 dated Apr. 5, 2018, 2 pages.
Patent Examination Report issued in Australian Application No. 2012364908, dated Jul. 23, 2016, 4 pages.
Peeters et al., "Ultrasonic Measurements of Coagulation and Fibrinolysis". J. Clin. Pathol., May 1964; 17:320-3. PubMed P.M.I.D.: 14159472; PubMed Central P.M.C.I.D.: PMC480759.
Petition For Inter Partes Review Of U.S. Pat. No. 9,272,280 B2, 28 Pages.
Petition For Inter Partes Review Of U.S. Pat. No. 9,410,971 B2, 51 Pages.
Petition For Inter Partes Review Of U.S. Pat. No. 9,410,971, dated Nov. 30, 2017, 74 pages.
Decision Denying Petitioner's Request for Rehearing for Inter Partes Review of U.S. Pat. No. 9,410,971, entered Nov. 3, 2017, 7 pages.
Patent Owner's Response to the Decision to Institute Inter Partes Review of U.S. Pat. No. 9,410,971, entered Dec. 1, 2017, 59 pages.
Declaration of Dr. Scott Diamond, Ph.D., dated Dec. 1, 2017.
Price et al., "Prognostic Significance of Post-Clopidogrel Platelet Reactivity Assessed by a Point-ofCcare Assay on Thrombotic Events after Drug-Eluting Stent Implantation". Eur. Heart J., Apr. 2008; 29(8):992-1000. PubMed P.M.I.D.: 18263931.
Prisco et al. "Point-of-Care Testing of Hemostasis in Cardiac Surgery". Thromb. J. May 6, 2003; 1(1):1, 10 pages. PubMed P.M.I.D.: 12904262; PubMed Central P.M.C.I.D.: PMC166118.
Rugeri et al."Diagnosis of early coagulation abnormalities in trauma patients by rotation thrombelastography", Journal of Thrombosis and Haemostasis, 5, 2007, pp. 289-295.
Rumbaut et al. "Platelet-Vessel Wall Interactions in Hemostasis and Thrombosis" (2010), San Rafael (CA): Morgan & Claypool Life Sciences, 5 pages.
Ruzicka, K., et al. Evaluation of Bedside Prothrombin Time and Activated Partial Thromboplastin Time Measurement by Coagulation Analyzer COAGUCHECK PLUS in Various Clinical Settings. Throm. Res., 87(5)1997 pp. 431-440. See also, Hillman, R., 1988 U.S. Pat. No. 4,756,884. Capillary Fill Device.
S. Kozek-Langenecker, Intensive Care Medicine, Annual Update 2007, Monitoring of Hemostasis in Emergency Medicine, pp. 847-860, Springer New York.
Scharbert et al., "Evaluation of the Platelet Mapping Assay on Rotational Thromboelastometry ROTEM". Platelets. Mar. 2009;20(2):125-30. PubMed P.M.I.D. 19235055.
Schochl et al., "Use of rotation thromboelastometry (ROTEM) to achieve successful treatment of polytrauma with fibrinogen concentrate and prothrombin complex concentrate", Anaesthesia, 2010, 65, pp. 199-203.
Taborski et al., "Analytical Performance of the New Coagulation Monitoring System INRatio for the Determination of INR Compared with the Coagulation Monitor Coaguchek S and an Established Laboratory Method" J. Thromb.Thrombolysis. Oct. 2004; 18(2):103-7. PubMed P.M.I.D.: 15789176.
Third party observation filed in European Patent Application No. 11766842.6, dated Mar. 6, 2016, 10 pages.
Third party observation filed in U.S. Appl. No. 15/202,059, filed Nov. 30, 2016, 40 pages.
Third party observation filed in U.S. Appl. No. 15/202,059 Application No. 12865280.7 (EP2676136), dated Nov. 23, 2016, pp. 1-4.
Tripodi et al., "International Sensitivity Index Calibration of the Near-Patient Testing Prothrombin Time Monitor, ProTime". Am. J. Clin. Pathol., Feb. 2003;119(2):241-5. PubMed P.M.I.D.: 12579994.

(56) References Cited

OTHER PUBLICATIONS

Versteeg et al., "New Fundamentals in Hemostasis", Physiol. Rev. Jan. 2013; 93(1):327-58. Review. PubMed P.M.I.D.: 23303912.
Wolff et al., "Aspirin for the Primary Prevention of Cardiovascular Events: an Update of the Evidence for the U.S. Preventive Services Task Force". Ann. Intern. Med., Mar. 17, 2009; 150(6):405-10. Review. PubMed P.M.I.D.: 19293073.
Examination Report issued in Australian Application No. 2012364908, dated Jun. 27, 2017, 5 pages.
Trial Board Order For Inter Partes Review Of U.S. Pat. No. 9,272,280 B2, 13 pages.
Trial Board Order For Inter Partes Review of U.S. Pat. No. 9,410,971 B2, 27 pages.
Office Action received in U.S. Appl. No. 15/357,492, dated Jun. 22, 2017.
Office Action received in co-pending U.S. Appl. No. 15/202,059, dated Oct. 4, 2016.
Office Action received in co-pending U.S. Appl. No. 15/202,059, dated Jul. 13, 2017.
Advisory Action received in co-pending U.S. Appl. No. 15/202,059, dated Sep. 21, 2017.
Office Action received in co-pending U.S. Appl. No. 15/202,059, dated Jan. 12, 2018.
Office Action received in co-pending U.S. Appl. No. 15/644,124, dated Sep. 7, 2017.
Office Action received in co-pending U.S. Appl. No. 15/644,124, dated Nov. 29, 2017.
Office Action received in co-pending U.S. Appl. No. 15/644,124, dated Feb. 6, 2018.
Patent Owner's Response to the Decision to Institute Inter Partes Review of U.S. Pat. No. 9,272,280, dated Dec. 1, 2017, 39 pages.
Declaration of Patrick D. Mize, Ph.D., dated Nov. 30, 2017.
Table of Prior Art Devices.
Görlinger, K., et al., "Perioperative Coagulation Management and Control of Platelet Transfusion by Point-of-Care Platelet Function Analysis," Transfus Med Hemother 34:396-411 (2007).
Rahe-Meyer, N. et al., Multicentric comparison of single portion reagents and liquid reagents for thromboelastometry. Blood Coagul Fibrinolysis Apr. 2009;20(3):218-22. PubMed P.M.I.D.: 19657320.
Stony Brook Portable Field Viscometer (For a quick 'Pass' or 'Fail' decision).
Faulds, D. et al., "Abciximab (c7E3 Fab). A review of its pharmacology and therapeutic potential in ischaemic heart disease; Drugs 583-98 (1994)" PubMed P.M.I.D.: 7528131 ("Faulds 1994").
Hemostasis and Thrombosis, Basic Principles and Clinical Practice. 3rd Edition. Eds. Colman R.W., Hirsh J., Marder V.J., Salzman E.W. (J.B. Lippincott Company, Philadelphia). Chapter 1 "Overview of Hemostasis" by R.W. Colman, V.J. Marder, E.W. Salzman, J. Hirsh. pp. 3-18. 1994.
Wolberg AS. Plasma and cellular contributions to fibrin network formation, structure and stability. Haemophilia. May 16, 2010:7-12.
Janus TJ, Lewis SD, Lorand L, Shafer JA. Promotion of thrombin-catalyzed activation of factor XIII by fibrinogen. Biochemistry. 1983;22(26):6269-72.
Niewiarowski S, Stewart GJ, Nath N, Sha AT, Lieberman GE. ADP, thrombin, and Bothrops atrox thrombinlike enzyme in platelet-dependent fibrin retraction. The American journal of physiology. 1975;229(3):737-45.
Janmey PA, Erdile L, Bale MD, Ferry JD. Kinetics of fibrin oligomer formation observed by electron microscopy. Biochemistry. 1983;22(18):4336-40.
Blättler W, Straub PW, Peyer A. Effect of in vivo produced fibrinogen-fibrin intermediates on viscosity of human blood. Thrombosis research. 1974;4(6):787-801.
Weisel JW. The mechanical properties of fibrin for basic scientists and clinicians. Biophysical Chemistry. 2004;112(2-3):267-276.
Cuisset T, Frere C, Poyet R, et al. Clopidogrel response: Head-to-head comparison of different platelet assays to identify clopidogrel non-responder patients after coronary stenting. Archives of Cardiovascular Diseases. 2010;103(1):39-45.

Multiplate® Analyzer Product Guide.
VerifyNow® Product Guide.
Kuntamukkula MS, McIntire L V, Moake JL, Peterson DM, Thompson WJ. Rheological studies of the contractile force within platelet-fibrin clots: effects of prostaglandin E1, dibutyryl-cAMP and dibutyryl-cGMP. Thrombosis research. 1978;13(6):957-69.
Plotkin, et al., The Journal of Trauma: Injury, Infection, and Critical Care. 2008.
Fundamentals of biomechanics Equiolobrium, Motion, and Deformation. 2nd Edition. Eds. Nihat Özkaya and Margareta Nordin. (Springer Science+Business Media, Inc., New York, NY). Chapter 9 "Mechanical Properties of Biological Tissues." pp. 196-218. 1999.
Instrument Engineers' Handbook. Fourth Edition. Ed. Bela G. Liptak (CRC Press). Process Measurement and Analysis vol. 1, Chapter 8 Analytical Instrumentation. 8.53 Rheometers, 1628-1636, 2003.
Thurston GB. Viscoelasticity of Human Blood. Biophysical Journal. 1972; 12:1205-1217.
Webster, Medical Instrumentation: Application and Design, New York: John Wiley & Sons, 1998, 6 pages.
Patent Owner's Preliminary Response to Petition Requesting Inter Partes Review of U.S. Pat. No. 9,410,971, dated Feb. 14, 2018, 33 pages.
Petitioner's Reply to Patent Owner's Response of U.S. Pat. No. 9,272,280 dated Mar. 1, 2018, 17 pages.
Petitioner's Reply to Patent Owner's Response of U.S. Pat. No. 9,410,971 dated Mar. 1, 2018, 25 pages.
Lang et al., "Possibilities and limitations of thromboeleastometry/thromboelastography," Downloaded from www.haemostaseologie-online.com on Mar. 6, 2018 | IP: 24.163.60.123.
Notice of Allowance issued for U.S. Appl. No. 15/202,059, dated May 23, 2018.
Corrected Notice of Allowance issued for U.S. Appl. No. 15/202,059, dated Jun. 22, 2018.
Examination Report issued for Australian Application No. 2017248548, dated Jul. 9, 2018.
Office Action issued for U.S. Appl. No. 15/904,984, dated Jul. 12, 2018.
Office Action issued for Canadian Application No. 2,823,729, dated Mar. 9, 2018.
Office Action issued for Canadian Application No. 2,823,729, dated Nov. 14, 2018.
Office Action issued for Canadian Application No. 2,823,729, dated Aug. 14, 2019.
Office Action issued for Canadian Application No. 2,823,729, dated Apr. 6, 2020.
Office Action issued for Canadian Application No. 2,826,770 dated Feb. 1, 2019, 4 pages.
Office Action issued for Chinese Application No. 2017101635956, dated Jul. 17, 2018.
Office Action issued for Chinese Application No. 2017101635956, dated Apr. 26, 2019.
Office Action issued for Chinese Application No. 2017101635956, dated Sep. 27, 2019.
Notice of Grant issued for Chinese Application No. 2017101635956, dated Jan. 13, 2020.
Fricke, W., Kouides, P., Kessler, C., Schmaier, A.H., Krijanovski, Y., Jagadeesen, K., Joist, J., A multicenter clinical evaluation of the Clot Signature Analyzer. J. Thromb. Hasemostasis. 2004; 2:763-8.
Shore-Lesseron., Evidence Based Coagulation Monitors: Heparin Monitoring, Thromboelastography, and Platelet Function. Sem. Cardiothoracic Vasc. Anesthesia., Mar. 2005; 9(1):42-52.
Moake J Overview of Hemostasis. Merck Manuals 2016 http://www.merckmanuals.com/professional/hematology-and-oncology/hemostasis/overview-of-hemostasis.
Theusinger, O.M., Nürnberg, J., Asmis, L.M., Seifert, B., Spahn, D.R., Rotation thromboelastometry (ROTEM) stability and reproducibility over time. Eur. J. Cardiothorac. Surg. 2010;37:677-83.
Tomauiolo, M., Brass, L.F., Stalker, T.J., Regulation of Platelet Activation and Coagulation and Its Role in Vascular Injury and Arterial Thrombosis. Interv. Cardiol. Clin. Jan. 2017; 6(1):1-12.
Fundamentals of biomechanics Equiolobrium, Motion, and Deformation. 3rd Edition. Eds. Nihat Özkaya and Margareta Nordin.

(56) References Cited

OTHER PUBLICATIONS (Springer Science+Business Media, Inc., new York, NY). Chapter 15 "Mechanical Properties of Biological Tissues." pp. 221-236. 2012.
Conduct of Proceeding For Inter Partes Review of U.S. Pat. No. 9,272,280 B2 dated Apr. 26, 2018, 3 pages.
Petitioner's Supplemental Reply For Inter Partes Review of U.S. Pat. No. 9,272,280 B2 dated May 18, 2018, 10 pages.
Conduct of Proceeding For Inter Partes Review of U.S. Pat. No. 9,410,971 dated Apr. 26, 2018, 3 pages.
Conduct of Proceeding For Inter Partes Review of U.S. Pat. No. 9,410,971 dated May 24, 2018, 5 pages.
Trial Paper For Inter Partes Review of U.S. Pat. No. 9,272,280 B2 dated Jul. 11, 2018, 10 pages.
Trial Paper For Inter Partes Review of U.S. Pat. No. 9,410,971 dated Jul. 11, 2018, 10 pages.
Trial Paper For Inter Partes Review of U.S. Pat. No. 9,410,971 dated Aug. 28, 2018, 3 pages.
Petition for Inter Partes Review For U.S. Pat. No. 9,915,671 dated Apr. 20, 2018, 76 pages.
Patent Owner's Preliminary Response for Inter Partes Review for U.S. Pat. No. 9,915,671 dated Jul. 20, 2018, 14 pages.
Weiss HJ, Aledort LM, Kochwa S., The effect of salicylates on the hemostatic properties of platelets in man. J Clin Invest. Sep. 1968;47(9):2169-80.
Trial Paper For Inter Partes Review of U.S. Pat. No. 9,410,971 dated Oct. 2, 2017, 11 pages.
Trial Paper For Inter Partes Review of U.S. Pat. No. 9,410,971 dated Dec. 1, 2017, 4 pages.
Declaration of Scott Diamond For Inter Partes Review of U.S. Pat. No. 9,915,671 dated Apr. 20, 2018, 200 pages.
Final Written Decision For Inter Partes Review of U.S. Pat. No. 9,410,971, dated Feb. 13, 2019, 55 pages.
Declaration of John Avila For Inter Partes Review of U.S. Pat. No. 9,915,671, dated Jan. 4, 2019, 38 pages.
Decision to Institute For Inter Partes Review of U.S. Pat. No. 9,915,671, dated Oct. 5, 2018, 27 pages.
Patent Owner's Response For Inter Partes Review of U.S. Pat. No. 9,915,671, dated Jan. 4, 2019, 37 pages.
Declaration of Frank M. Laduca, Ph.D, dated Feb. 21, 2019, 117 pages.
Petition for Post-Grant Review of U.S. Pat. No. 9,977,039, dated Feb. 21, 2019, 95 pages.
Final Written Decision For Inter Partes Review of U.S. Pat. No. 9,272,280, dated Feb. 13, 2019, 25 pages.
Nielson V, A Comparison of the Thrombelastograph and ROTEM, Blood Coagulation and Fibrinolysis 18:3, 247-252, 2007.
Declaration of Frank M. Laduca, Ph.D., FAHA, dated Apr. 24, 2019, 130 pages.
Hanecke, P and Klouche, M, Thrombelastography Today: Practicability and Analytical Power, Transfusion Medicine and Hemotherapy. 34. 421-428 (2007) ("Hanecke").
The 510(k) Summary for ROTEM delta, FDA clearance No. K083842 ("the 510(k) Summary for ROTEM delta").
The 510(k) Substantial Equivalence Determination Decision Summary for ROTEM delta, FDA clearance No. K083842 (the "Decision Summary for ROTEM delta").
User Manual (2007) for TEG 5000 Thrombelastograph Hemostasis System with TEG Analytical Software (TAS) Version 4.2.3 including an addendum (2008) for TEG Analytical Software (TAS) Version 4.3 (the "TEG 5000 User Manual").
*Instrumentation Laboratory Co.* v. *HemoSonics LLP*, IPR2017-00852, Paper No. 47 (PTAB Feb. 13, 2019) ("'852 FWD").
*Instrumentation Laboratory Co.* v. *HemoSonics LLP*, IPR2017-00855, Paper No. 55 (PTAB Feb. 13, 2019) ("'971 FWD").
Petition for Post-Grant Review of U.S. Pat. No. 10,031,144, dated Apr. 24, 2019, 104 pages.
Patent Owner's Notice of Appeal Inter Partes Review Case No. IPR2018-00950 U.S. Pat. No. 9,915,671B2, dated Feb. 4, 2020, 68 pages.
Wilson, D, et al. "Changes in Coagulability as Measured by Thrombelastography Following Surgery for Proximal Femoral Fracture." Injury, vol. 32, No. 10, 2001, pp. 765-770., doi:10.1016/s0020-s1383(01)00139-5. (Year: 2001).
Office Action issued for U.S. Appl. No. 15/641,731, dated Apr. 20, 2020.
Office Action issued for U.S. Appl. No. 15/641,731, dated Sep. 27, 2019.
Office Action issued for Canadian Application No. 2,795,454, dated Feb. 1, 2017.
Office Action issued for Canadian Application No. 2,795,454, dated Nov. 27, 2017.
Office Action issued for Canadian Application No. 2,795,454, dated Oct. 26, 2018.
Office Action issued for Canadian Application No. 2,795,454, dated Oct. 15, 2019.

NORMAL

| CF | FF | PF | LF |
|---|---|---|---|
| COAGULATION FACTOR FUNCTION | FIBRINOGEN FUNCTION | PLATELET FUNCTION | FIBRINOLYTIC FUNCTION |

FIG. 3A

REDUCED COAG FACTORS FUNCTION

| CF | FF | PF | LF |
|---|---|---|---|
| COAGULATION FACTOR FUNCTION | FIBRINOGEN FUNCTION | PLATELET FUNCTION | FIBRINOLYTIC FUNCTION |

FIG. 3B

REDUCED PLATELET FUNCTION

| CF | FF | PF | LF |
|---|---|---|---|
| COAGULATION FACTOR FUNCTION | FIBRINOGEN FUNCTION | PLATELET FUNCTION | FIBRINOLYTIC FUNCTION |

FIG. 3C

INCREASED FIBRINOLYTIC FUNCTION

| CF | FF | PF | LF |
|---|---|---|---|
| COAGULATION FACTOR FUNCTION | FIBRINOGEN FUNCTION | PLATELET FUNCTION | FIBRINOLYTIC FUNCTION |

FIG. 3D

REDUCED COAGULATION FACTORS AND PLATELET FUNCTION

| CF | FF | PF | LF |
|---|---|---|---|
| COAGULATION FACTOR FUNCTION | FIBRINOGEN FUNCTION | PLATELET FUNCTION | FIBRINOLYTIC FUNCTION |

FIG. 3E

INCREASED COAG FACTORS FUNCTION

| CF | FF | PF | LF |
|---|---|---|---|
| COAGULATION FACTOR FUNCTION | FIBRINOGEN FUNCTION | PLATELET FUNCTION | FIBRINOLYTIC FUNCTION |

FIG. 3F

HEMOSTATIC PARAMETER DISPLAY

CROSS-REFERENCE TO RELATED APPLICATIONS

The present application is a continuation application of U.S. patent application Ser. No. 13/083,360, filed Apr. 8, 2011, entitled "Hemostatic Parameter Display," now U.S. Pat. No. 10,147,152, which claims priority to, and the benefit of, U.S. provisional patent application No. 61/322, 049, filed on Apr. 8, 2010, and entitled "Novel Technology for Point-of-Care Assessment of Hemostasis", each of which is incorporated by reference herein in its entirety.

ACKNOWLEDGEMENT OF GOVERNMENT SUPPORT

This invention was made with government support under Grant Nos. R43 HL103030 and R44-DK085844 awarded by the National Institutes of Health. The Government has certain rights in the invention.

FIELD OF THE INVENTION

The present invention relates to displays for physiologic parameters and more particularly displays with graphical user interfaces (GUI) for intuitively presenting physiologic parameters for easy use and interpretation by healthcare personnel.

BACKGROUND

The formation of a blood clot and its successive dissolution, referred to as the hemostatic process, is required to arrest blood loss from an injured vessel. This process is the result of a delicate functional balance between plasma coagulation factors (including fibrinogen), platelets, and fibrinolytic proteins. Each of these elements plays an important role in activating/deactivating the others, and the appropriate stimuli are necessary to prevent excessive blood loss without causing inappropriate thrombosis, see Laposata M., et al., The Clinical Hemostasis Handbook, Year Book Medical Publisher 1989.

The hemostatic process is initiated by the activation and subsequent adhesion of platelets to the site of injury within the vessel wall. Activated platelets recruit other platelets and interact with fibrinogen in the blood plasma via the glycoprotein IIb/IIIa receptor to form a platelet-plug that serves as the initial response to stop blood loss. Hemostasis then proceeds with a cascade of proteolytic reactions of the plasma coagulation proteins that ultimately form a three-dimensional network of fibrin that strengthens the platelet-plug. The fibrin chains are cross-linked and stabilized by the plasma factor XIIIa (FXIIIa). Platelets also have a central role in regulating the process of fibrin polymerization. The final step of hemostasis (i.e., fibrinolysis) involves the activation of the plasma protein plasmin, which dissolves the blood clot when its useful life is over. This cell-based model of hemostasis closely reflects the in vivo physiological process, e.g., see Hoffman et al., "A cell-based model of hemostasis;" Thromb. Haemost. 2001; 85:958-965 and Becker, "Cell-Based Models of Coagulation: A Paradigm in Evolution;" J. Thromb. Thrombolysis 2005: 20:65-68.

The mechanical properties of blood clots have implications for its function of stopping blood loss. Alterations in clot structure and its underlying mechanical properties have been implicated in thrombotic disease and other life threatening pathologies, see Weisel, J. W., "Enigmas of Blood Clot Elasticity;" Science 2008; 320:456. Recently, it was shown that fibrin clots of patients affected by premature coronary artery disease have a different structure and higher stiffness compared to the fibrin clots of healthy age-matched controls, see Collet et al, "Altered Fibrin Architecture is Associated with Hypofibrinloysis and Premature Coronary Atherothrombosis;" Arterioscler. Thromb. Vasc. Biol. 2006; 26:2567-2573.

The mechanics of fibrin networks have been studied extensively at the macroscopic level see Ryan et al., "Structural Origins of Fibrin Clot Rheology"; Biophys. J. 1999; 77:2813-2826 and Jen et al., "The Structural Properties and Contractile Force of a Clot;" Cell Motil. 1982; 2:445-455. The viscoelastic properties of individual fibrin strands have also been investigated by means of AFM (see Liu et al., "Fibrin Fibers Have Extraordinary Extensibility and Elasticity;" Science 2006; 313:634) and "optical tweezers," see Collet et al., "The elasticity of an individual fibrin fiber in a clot;" Proc. Natl. Acad. Sci. USA 2005; 102:9133-9137.

Disruption of the hemostatic balance plays a role in the onset of potentially fatal conditions, including myocardial infarction, stroke, deep vein thrombosis, pulmonary embolism, and excessive bleeding, see Hoyert et al., "Deaths: preliminary data for 2003", Natl. Vital Stat. Rep. 2005; 53:1-48 and Hambleton et al., "Coagulation: Consultative Hemostasis"; Hematology 2002; 1:335-352. These conditions account for over 30% of all deaths in the developed world. The ability to recognize and quantify defects of the hemostatic process may reduce mortality and implement appropriate treatment.

Further improvements in the detection and treatment of hemostatic defects are therefore desired.

SUMMARY

In one embodiment, the present invention includes a system for displaying one or more of a plurality of hemostatic indexes, the system having a communication receiver and a GUI. The communication receiver is configured to receive the hemostatic indexes. The GUI is connected to the communication receiver and configured to display one, or simultaneously at least two, of the hemostatic indexes. The hemostatic indexes are derived from one or more of a plurality of independent measurements.

In one example, one of the indexes may be calculated from two of the independent measurements, such as from ultrasound measurements on two sample wells containing different reagents.

The hemostatic indexes may include a coagulation factor function, a fibrinogen concentration, a fibrinogen function, a platelet function and a fibrinolysis function. The coagulation factor may include at least one of an intrinsic activiation factor or an extrinsic activation factor. The GUI may be further configured to display hematocrit, hemoglobin concentration and red cell count simultaneously with the two hemostatic indexes.

Also, the GUI may be configured to display the functional hemostasis indexes as a numerical score or a graphical depiction or with varying colors.

In another embodiment, the GUI is further configured to display a history of the hemostatic indexes and clinical interventions overlaid on the history. At least one portion of the history may include an array of graphical indicators, with each of the graphical indicators representing one of the hemostatic indexes at some time in the history. The graphical indicators may have a relative positioning configured to communicate a hemostatic condition of the subject at that time in history.

In yet another embodiment, the GUI may be further configured to display a treatment recommendation based on the at least two hemostatic indexes. For example, the treatment recommendation may be guiding transfusion of platelets, cryoprecipitate, plasma, red cells or antifibrinolytics. Or, the treatment recommendation is for guiding therapies of at least one of an anti-platelet drug, anti-coagulant drug or pro-fibrinolysis drug.

In another embodiment, a method includes deriving a plurality of hemostatic indexes from a plurality of independent measurements and displaying at least two of the hemostatic indexes.

In another embodiment, a system for measuring hemostatic characteristics of a blood sample includes a processor and a GUI. The processor is configured to receive a data stream of stiffness measurements of the blood sample and to estimate a possible range of a functional hemostatic index based on the data stream. The GUI is connected in communication with the processor and is configured to display the possible range of the functional hemostatic index.

Also, the processor may be configured to determine changes in the possible range as new data is received from the data stream and the GUI is configured to dynamically adapt a graphical element to express those changes.

Advantages of embodiments of the present invention include the ability to show two or more hemostatic indexes at the same time wherein the prior art is limited to serial tests. Another advantage is the ability for healthcare personnel to see the past history of various hemostatic indexes and the impact of various treatments. Additionally, healthcare personnel may benefit from display of trends in the hemostatic indexes and are able to more quickly apply preventive treatment in urgent care situations.

BRIEF DESCRIPTION OF THE SEVERAL VIEWS OF THE DRAWINGS

FIGS. 3A-3F show a plurality of GUI display configurations of the system of FIG. 1 indicating different patient conditions;

DETAILED DESCRIPTION

Figure 1:
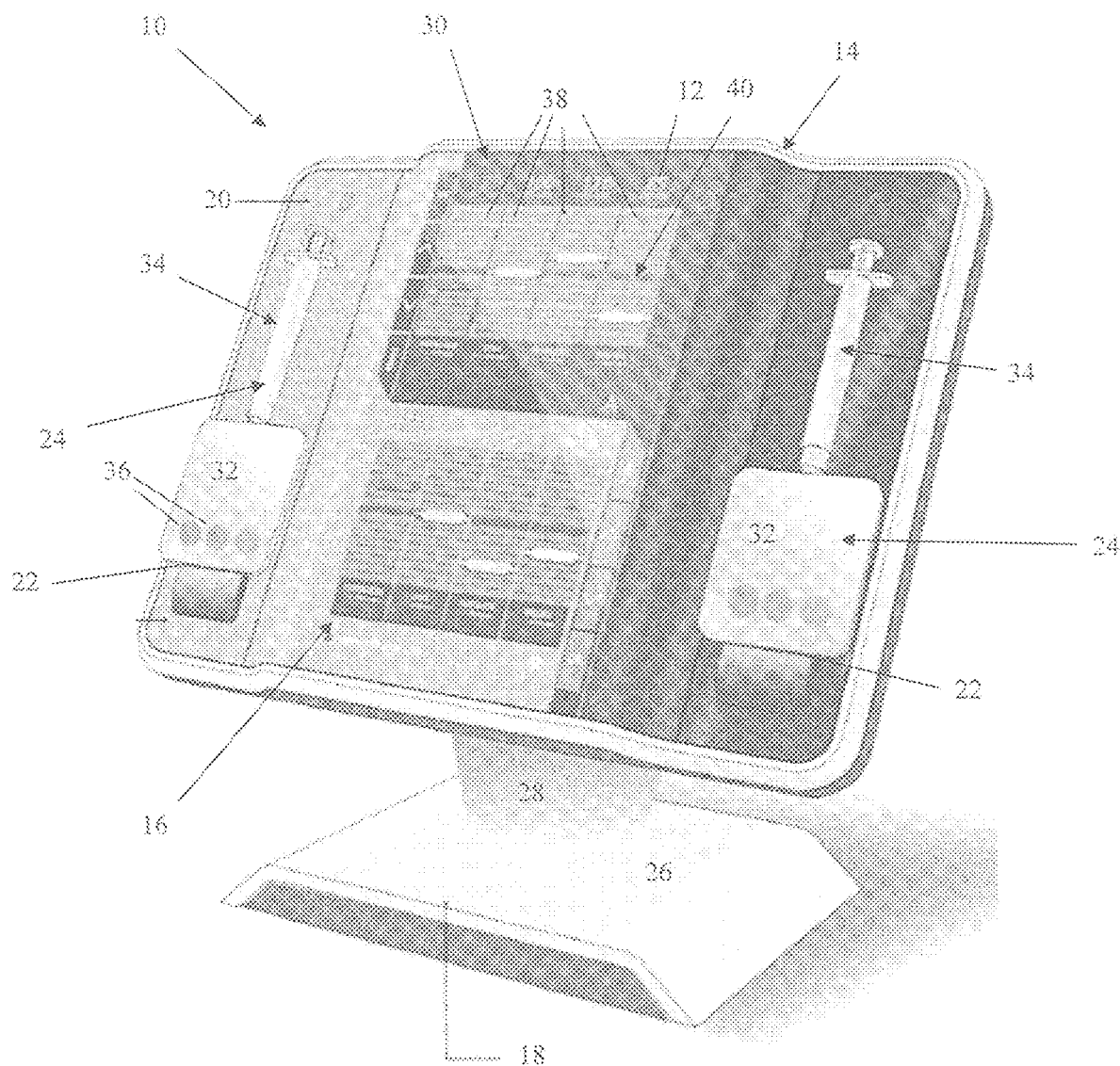
FIG. 1 is a perspective view of a functional hemostatic index determination and display system.

The inventors have made the following observations. Unregulated hemostasis, manifested either as thrombotic disease or excessive bleeding, represents one of the leading causes of morbidity and mortality in the developed world. For example, millions of patients in the United States are currently prescribed anti-platelet medications (such as aspirin or clopidogrel) or anti-coagulation drugs (such as coumadin, heparin or direct thrombin inhibitors) to prevent the occurrence of thrombotic conditions. However, it has been estimated that 5-60% of these patients may not respond adequately to aspirin and 4-30% to clopidogrel, for example, leading to higher risks of recurring thrombotic events or excessive bleeding.

Excessive bleeding often occurs during trauma, major surgical procedures, and on the battlefield. In these cases, transfusion of blood and its derived products are used in clinical practice to manage excessive bleeding. Generally, there are four treatment options available, each corresponding to a specific hemostatic defect: (a) fresh frozen plasma (FFP) to restore the plasma coagulation proteins, (b) platelet concentrate to restore platelets, (c) cryoprecipitate to restore fibrinogen, and (d) anti-fibrinolytics to slow the activity of the clot-dissolving proteins. Additionally, packed red blood cells (RBCs) are administered if hematocrit or hemoglobin falls within a certain threshold level.

While transfusions of blood products have had a great impact in saving lives, blood and its derived products are scarce and have to be carefully optimized. Furthermore, transfusion therapies carry the risks of possible allergic reactions, a variety of viral and bacterial infections, and worsened outcomes. The use of blood products is particularly intensive in cardiac surgery involving cardio-pulmonary bypass (CPB), where over 60% of patients experience excessive intra and post-operative bleeding.

It has been estimated that CPB surgeries account for roughly 20% of the total blood products used in the United States, with significant variations in protocols and guidelines among different institutions. Intra- and post-operative bleeding in CPB is often the result of blood being heavily anti-coagulated and exposed to the foreign surfaces of the extracorporeal circuitry. Loss of platelets, abnormal platelet function, hemodilution, inadequate function of the fibrinolytic system, and patients' cooling/warming also contribute to failure of the hemostatic system, which has to be corrected with allogenic blood products.

Several protocols and guidelines have been developed in the past years to optimize transfusion therapies in order to minimize the likelihood of negative outcomes, save valuable resources, and generate financial savings to the healthcare systems. Chief among those is a recent report from The Society of Thoracic Surgeons Blood Conservation Guideline Task Force in combination with The Society of Cardiovascular Anesthesiologists Special Task Force on Blood Transfusions. One of the key components of these protocols regards the use of POC diagnostic tests of coagulation and platelet function to recognize abnormalities of the hemostatic process. In clinical practice, however, empirical approaches are often used, and transfusions are administered with little or no quantitative guidance. Table I below summarizes some of the available treatments.

TABLE I

|  | Bleeding Patient | Clotting Patient |
| --- | --- | --- |
| Problem with Coagulation Factors | Transfuse Fresh Frozen Plasma | Administer Anti-coagulant (coumadin, heparin, direct thrombin inhibitor, etc) |
| Problem with Fibrinogen | Transfuse Cryoprecipitate | N/A |
| Problem with Platelets | Transfuse Platelets | Administer Anti-platelet therapy (aspirin, Plavix, etc) |
| Problem with Fibrinolysis | Administer Anti-fibrinolytic (aminocaproic acid or tranexamic acid, etc) | Administer Pro-fibrinolysis (tissue plasminogen activator, etc) |

Current tests of hemostasis can be divided into three broad categories: endpoint biochemical assays, mechanical/viscoelastic analyzers, and platelet-specific tests. Endpoint assays are traditionally performed on blood plasma and include such tests as the pro-thrombin time (PT/INR), activated partial thromboplastin time (aPTT), and the activated clotting time (ACT). A variety of methodologies, ranging from optical detection to flow impediment, are employed to determine the time required to reach a pre-defined endpoint that represents the clotting time. The output of these tests is generally the clotting time expressed in seconds (or minutes) or a single number selected from an arbitrary scale such as in the case of the INR (International Normalized Ratio).

While each of these assays measures a different aspect of the coagulation factors, even in combination they do not provide a complete representation of overall hemostasis. See, Gravlee et al., "Predictive value of blood clotting tests in cardiac surgical patients"; Ann. Thorac. Surg. 1994; 58:216-221 and Bajaj et al., "New insights into how blood clots: Implication for the use of APTT and PT as coagulation screening tests and in monitoring anticoagulant therapy"; Semin. Thromb. Hemost. 1999; 25:407-418.

Fibrinogen level, for example, is typically measured using the standard Clauss method, another end-point assay. The clotting time of platelet free plasma is measured in the presence of thrombin and compared to a calibration curve to determine fibrinogen level. The output of this test is the concentration of fibrinogen, typically expressed in units of mg/dl. The end point tests are further limited by the absence of active platelets.

In contrast, mechanical methods, such as the TEG® (Haemoscope), ROTEM® (Pentapharm), HAS (Hemodyne) and SonoClot® (Sienco), measure the contribution of all the components of hemostasis in whole blood. These methods have been widely studied and shown to offer valuable clinical and scientific insights, see Ganter et al., "Coagulation Monitoring: Current Techniques and Clinical Use of Viscoelastic Point-of-Care Coagulation Devices"; Anesth. Analg. 2008; 106:1366-1374.

Existing mechanical methods, however, utilize complex and expensive mechanical transducers, resulting in instruments that are difficult to operate and to interpret. The output of these systems is generally a curve that describes the overall hemostatic process along with some numerical scores. Further, the large mechanical strains (in the range of 8% to 16%) applied to the blood samples have been shown to interfere with clot formation and limit sensitivity and speed of the measurements, see Evans et al., "Rheometry and associated techniques for blood coagulation studies"; Med. Eng. Phys. 2008; 30:671-679 and Burghardt et al., "Nonlinear viscoelasticity and thromboelastograph: Studies on bovine plasma clots"; Biorheology 1995; 32:621-630.

The most common platelet tests are the platelet count and platelet aggregation. In a healthy patient, platelet count is between 150K and 400K platelets per $mm^3$. Platelet aggregation measures the ability of platelets to stick together and form small clumps. These tests are typically performed in central laboratories using platelet rich plasma (PRP), even though whole blood assays have recently emerged. Limitations include the necessity to perform the measurements with anticoagulated blood, which does not represent actual physiology, and the long turn-around-times (>45 minutes) to obtain results from the central lab.

Embodiments of the present invention disclosed herein include systems and methods for intuitively displaying a plurality of functional hemostasis indexes that are directly related to the therapies available for both the hypo-coagulable (i.e., bleeding) and hyper-coagulable (i.e., clotting) patient. The term "hemostasis indexes" as used herein indicates a series of measures that are related to physiological components or parameters involved directly or indirectly in the physiological process of hemostasis (as opposed to raw mechanical parameters). Knowledge of the function of these physiological components of hemostasis can enable diagnostic decisions by healthcare professionals. For example, these functional hemostasis indexes may include: (1) coagulation factor function, (2) fibrinogen concentration and/or function, (3) platelet function and (4) fibrinolytic function. As discussed above, the inventors have also recognized that transfusion of packed red cells is common in a bleeding patient. Therefore, an additional hemostasis index represented by the hematocrit, hemoglobin concentration or red cell count so that the system can provide information about additional possible transfusion products.

In one embodiment, the hemostatic indexes are determined using sonorheometry. Coagulation factor function (when determined by sonorheometry) is the time at which significant fibrin formation occurs which is measured as the time at which clot stiffening starts. It is determined by finding the point on the time-stiffness curve where stiffness rises by an order of magnitude above baseline. Normal values are about 3.5 minutes with +/−10% or 0.35 minutes. Pathological values can fall as low as 1 minute.

Fibrinogen function (when determined by sonorheometry) is the maximum clot stiffness in the absence of platelet function. Either stiffness units or traditional mg/dL units may be used. It is determined as the maximum stiffness in a test well having kaolin plus ReoPro®. Normal values are $10^4$ in stiffness which corresponds to about 300 mg/dL. Normal variation is about +/−5%. Pathological values range from 15 mg/dL to above 450 mg/dL.

Platelet function (when determined by sonorheometry) is the multiplicative increase in clot stiffness that is attributed to platelets. It is determined by dividing the maximum stiffness in a test well with kaolin by the test well with kaolin plus ReoPro. It yields a dimensionless number that normally is 10+/−1 with pathological values ranging as low as 1.

Fibrinolytic function (when determined by sonorheometry) is the time at which fibrinolysis begins, and in some cases may include the effect of an accelerant. Without an accelerant, it is determined to be the point on the time-stiffness curve where stiffness falls by 50%. Normal is generally defined as 90 minutes with pathological values ranging as low as 10 minutes. An expected range is about 60 to 120 minutes based on prior experience.

With reference now to FIG. 1, embodiments of the present invention include a system 10 for displaying a plurality of hemostatic indexes 12. The system includes a communication receiver 14 configured to receive the hemostatic indexes 12 and a graphical user interface (GUI) 16 connected to the communication receiver 14 and configured to display one, or simultaneously at least two, of the hemostatic indexes 12. The hemostatic indexes 12 are derived from a plurality of independent measurements, such as the mechanical measurements determined using the sonorheometry systems and processes described in more detail below.

The term "GUI" or "graphical user interface" as used herein includes any hardware, software, firmware or combination thereof, or even non-electronic interfaces, capable of generating graphical depictions such as liquid-crystal displays, computer monitors, cell phone or PDA screens, televisions, tablet computers etc.

The term "independent measurement" as used herein refers to separate tests, sonorheometry or otherwise, which may be performed on a single sample, such as a series ultrasound tests using the same instrument, or on multiple samples, such as parallel tests by multiple instruments or sensors.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some embodiments of the present invention use an ultrasound-based technology ("sonorheometry") to quantify the dynamic changes in mechanical properties of whole blood during the process of coagulation and clot dissolution. This provides information about the role of the coagulation factors, fibrinogen, platelets, and fibrinolytic proteins to overall hemostatic function.

Sonorheometry uses the phenomenon of acoustic radiation force to make repeated viscoelastic measurements of a whole blood sample. Acoustic radiation force can be described as the transfer of momentum between an acoustic wave (or pulse) and a reflection or absorbing target. As a result of the transferred momentum, the target experiences a small unidirectional force in the direction of the wave (or pulse) propagation. For a perfect absorber, this can be mathematically defined as follows:

$$|\vec{F}| = \frac{2\alpha \langle I(t) \rangle}{c} = \frac{2\alpha PII}{c} PRF \qquad (1)$$

where $|\vec{F}|$ is acoustic radiation force (in units of $m^{-1}$), $\alpha$ is the attenuation coefficient of the medium, c (in units of m/s) is the speed of sound in the medium, I(t) (in units of $W/m^2$) is the instantaneous intensity of the beam (e.g., ultrasound beam), PII is pulse intensity integral, and PRF is pulse repetition frequency (typically measured in hertz), which characterizes the time interval between pulse or wave firings.

In order to exploit the acoustic radiation force phenomenon as a means to discern material properties of tissue, sonorheometry can be performed as a series of pulses transmitted so that the temporal characteristic of the acoustic radiation force approximates a step-function. In this stepwise radiation force that is applied, the resultant displacement profiles mimic responses observed in viscoelastic creep tests and can be described by viscoelastic models such as the Voigt or Kelvin models. Parameters such as steady-state displacement or time constants can be extracted which characterize material properties of the tissue that the acoustic force radiation is applied to. When the target tissue is whole blood, sonorheometry as described herein can be used to monitor coagulation and clot dissolution properties (i.e., the hemostatic process).

Sonorheometry is performed using acoustic radiation force as a means to generate small and localized displacements within a sample, e.g., a whole blood sample. Returned echoes are processed to measure the induced displacements and determine viscoelastic properties of the sample. In at least one embodiment, displacements are quantified using a principal component-based estimator technique, such as is described in Mauldin, Jr. et al., "Reduction of echo decorrelation via complex principal component filtering," Ultrasound Med. Biol., vol. 35, no. 8, pp. 1325-1343, 2009 and in U.S. application Ser. No. 12/467,216 filed May 15, 2009 and titled "Reduction of Echo Decorrelation in Ultrasonic Motion Estimation."

Figure 2A:
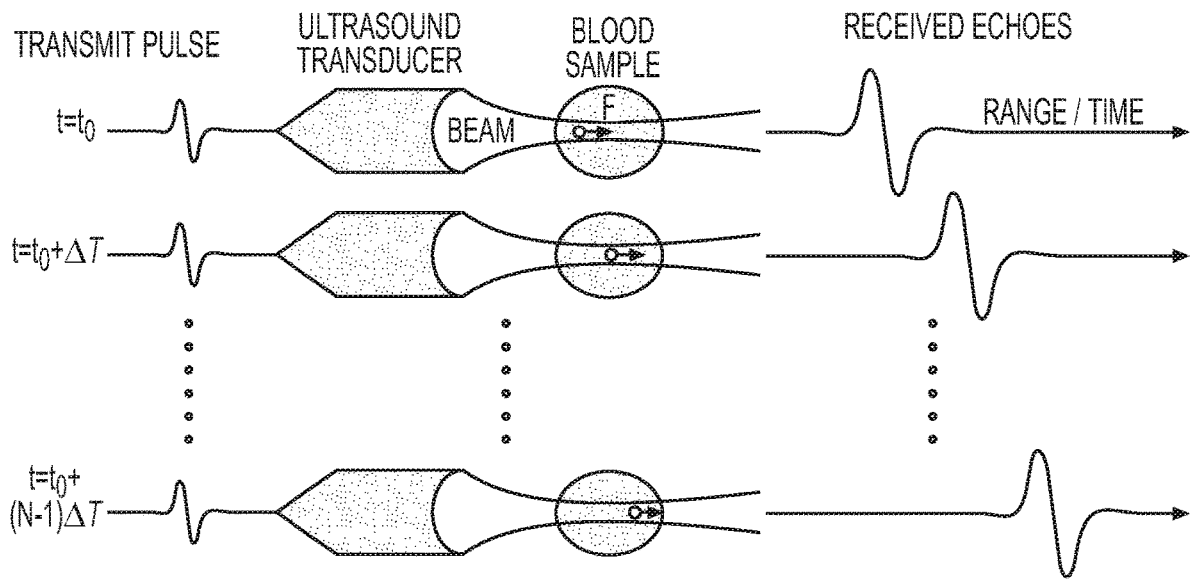
FIGS. 2A and 2B are diagrams of sonorheometry to determine the hemostatic indexes displayed in FIG. 1.

In performing sonorheometry according to the present invention, for each measurement a series of N ultrasound pulses (where N=a positive integer) are fired toward a specified location within a blood sample at time intervals $\Delta T$, e.g., see FIG. 2A. Each pulse generates radiation force as energy is absorbed and reflected during propagation. This radiation force induces displacements within the blood sample that depend upon local force application and mechanical properties of the blood. Each pulse also returns an echo as a portion of its energy is reflected from cell/plasma interfaces within the blood. Because the tissue (blood) moves slightly from one transmission to the next, the path length between the ultrasound transducer and any given region within the target (blood) changes with pulse number. This change in path length can be readily estimated from differences in the arrival times of echoes from the same region, thereby accomplishing motion tracking of the sample. The series of N acoustic pulses are sent into the blood sample at a specified pulse repetition frequency (PRF). These pulses generate acoustic radiation force that induces a deformation field within the sample. The deformation field can be estimated from the time delays of the N returning echoes.

The ensemble of the time delays forms a time-displacement curve that describes the viscoelastic properties of the sample being analyzed. This process is then repeated M times (where M is a positive integer), with intervening relaxation periods, to provide data about the dynamics of clot formation and dissolution. As blood coagulates reduction in displacement is observed. The values of the M steady-state displacements are combined to form a relative stiffness curve that is representative of the hemostatic process, e.g., see FIG. 2B. The stiffness parameter is referred to as "relative" since the absolute magnitude of the radiation force is unknown due to its dependency on blood acoustic properties which change throughout coagulation. Alternatively the changes in acoustic properties (i.e., changes in acoustic attenuation a and speed of sound c) can be measured using a known reflector so that acoustic radiation force can be calculated and absolute stiffness values can be calculated.

Figure 2B:
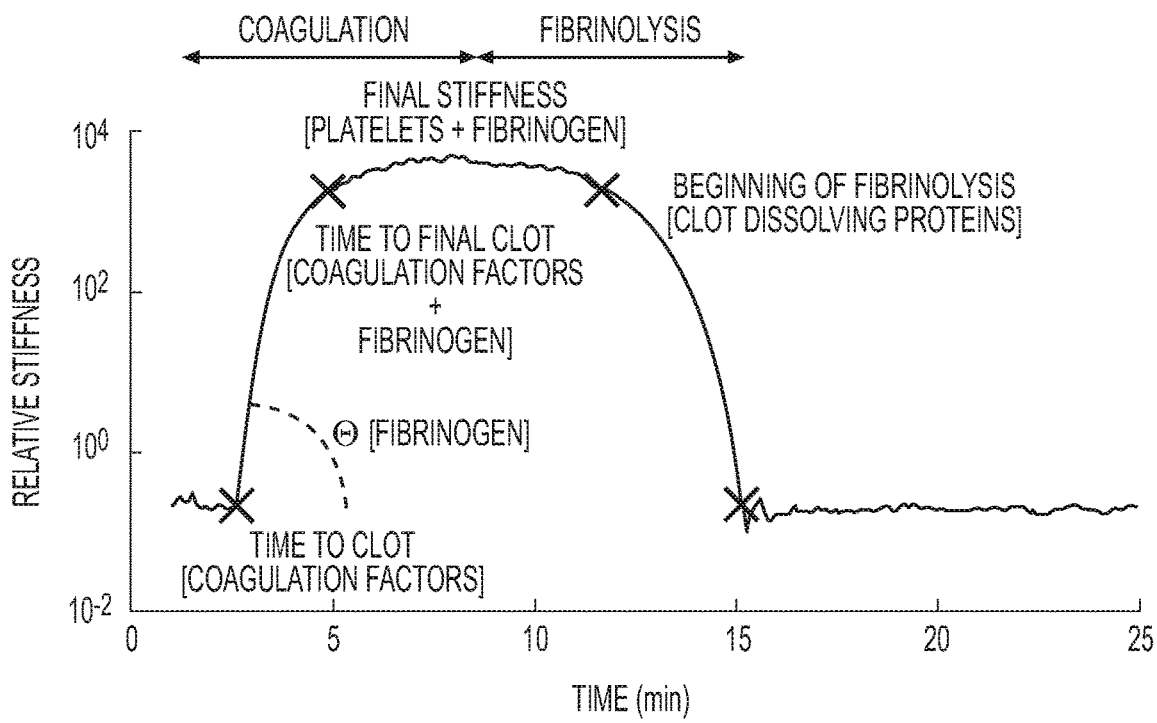

In FIG. 2B, the relative stiffness curve shows characteristic features labeled Time to Clot (TC1), Time to Final Clot (TC2), Angle (Θ), Final Stiffness (S), Beginning of Fibrinolysis (TL1) and End of Fibrinolysis (TL2). The hemostasis parameters indicated in FIG. 2B are calculated by first fitting the sonorheometry relative stiffness data to a modified sigmoidal function such as, for example, the following model (although other models may be alternatively used to accomplish these calculations, such as a combination of linear trends or a combination of skewed error functions):

$$f(t) = \alpha \frac{t^\beta}{1 + e^{-\left(\frac{t-\gamma}{\delta}\right)\sigma}} + \varepsilon \qquad (2)$$

where t is experimental time (in seconds) and $\alpha$, $\beta$, $\gamma$, $\delta$ and $\varepsilon$ are parameters determined to best fit the model curve to the data.

The parameter TC1 corresponds to the rapid increase in relative stiffness, indicating the beginning of fibrin polymerization. Similarly, the parameter TC2 represents the ending of fibrin polymerization. TC1 and TC2 are calculated based on a threshold value of the derivative curve of the relative stiffness (20% of the minimum value). The angle Θ is the slope of the relative stiffness during fibrin polymerization, which extends generally between TC1 and TC2. The angle, defined as the slope of the line between TC1 and TC2, is indicative of the rate of fibrin polymerization. The final stiffness S (maximum stiffness) corresponding to the maximum stiffness of the clot. The maximum stiffness S depends upon platelet function and the stiffness of the fibrin network. The times TL1 and TL2 can be defined to represent the initial and final phases of the fibrinolytic process and the consequent dissolution of the fibrin network (time to lysis). TL1, indicating the "lysis initiation time", and TL2, indicating the "end of lysis time", can be calculated by defining a new sigmoidal curve similar to that defined by equation (2), calculating the curve derivative, and estimating the times corresponding, for example, to twenty percent of the minimum of the derivative. A summary of the parameters generated is presented in Table II below:

TABLE II

| | | |
|---|---|---|
| $TC_1$, $TC_2$ | Measure initial and final fibrin formation | Function of fibrinogen and other coagulation factors |
| S | Fibrin and platelet activity | Function of fibrin network and platelet aggregation |
| Θ | Rate of fibrin polymerization | Function of fibrinogen and other coagulation factors |
| $TL_1$, $TL_2$ | Clot dissolving process | Function of fibrinolytic proteins of the plasma |

In order to isolate the four main components of hemostasis, four sonorheometry measurements can be performed in parallel using a combination of agonists and antagonists reagents. In a possible embodiment, test well 1 may have kaolin powder to activate coagulation through the intrinsic pathway. Test well 2 may have a combination of kaolin and abciximab (ReoPro) to inhibit platelet aggregation. Test well 3 may have abciximab and thrombin to activate coagulation through the common pathway. Test well 4 may have tissue factor to activate coagulation through the extrinsic pathway. In one embodiment, the measurements in each well can be combined to form hemostatic indexes as shown in the Table III below:

TABLE III

| | |
|---|---|
| Coagulation factors function (Intrinsic Pathway) | Time to clot $TC_1$ in well #1 |
| Coagulation factors function (Extrinsic Pathway) | Time to clot $TC_1$ in well #4 |
| Platelets function | Stiffness S differential between well #1 and well #2 |
| Fibrinogen function | Stiffness S in well #3 |
| Fibrinolysis function | Time to lysis $TL_1$ in well #4 |

The measurements of hematocrit (HCT), hemoglobin concentration (HGB) and red cell count (RBC) can be performed using ultrasound signals by methods such as those disclosed in U.S. Prov. Pat. App. No. 61/443,084 filed on Feb. 15, 2011 and entitled "CHARACTERIZATION OF BLOOD PARAMETERS INCLUDING HEMATOCRIT AND HEMOSTASIS," and hereby incorporated in its entirety by reference.

In other embodiments, the hemostatic indexes may be obtained for display from one or more diagnostic devices that provide information regarding the process of coagulation and fibrinolysis (i.e., the hemostatic process). Such devices include, for example, methods based on direct measurements of blood viscoelasticity such as the TEG® (Haemoscope), ROTEM® (Pentapharm), HAS (Hemodyne) and SonoClot® (Sienco).

Referring again to FIG. 1, the system 10 of the present invention includes a base 18, a housing 20 containing various electronic components and software such as the communication receiver 14, a pair of consumable receptacles 22 holding consumables 24, and the GUI 16.

The base 18 is constructed of a molded plastic and includes a foot 26 or flange for resting upon a flat surface, such as a patient's bedside, and a post 28 extending upwards therefrom to support the housing 20. Advantageously, the space between the bottom edge of the housing 20 and the top of the foot 26 provides room for resting a storage container of the consumables 24. The base 18 may also function as a passage for wiring, power, communication or otherwise, connecting to the electronics within the housing 20 or the GUI 16.

The housing 20 includes a plurality of walls in a rectangular arrangement that is supported by the post 28 of the base 18 in an inclined, near vertical orientation for easy viewing by and interaction with healthcare personnel. Contained within the housing 20 may be various combinations of hardware, software, firmware and other electronics to support the application of sonorheometry to the consumables 24, operation of the GUI 16 (such as through a video card or driver) and other functions.

For example, selected components of FIG. 19 (described in more detail below) may be included within the housing 20 to enable the functions and processes described herein. Alternatively, the housing 20 may only contain very basic components for displaying the results of sonorheometry. For example, the communication receiver 14 may be a video card or video driver, a wireless receiver or basic hardware and software for communicating with cloud-based or other distributed processing power to receive the hemostatic indexes 12 and other information.

The housing 20 includes a front screen 30 comprised of a transparent plastic that includes a central raised portion and a pair of lateral portions. The portions define planar surfaces. The lateral portions are on either side of the central raised portion and are recessed or spaced behind the central raised portion. The recessed position of the lateral portions provides clearance for the consumables 24 and defines the consumable receptacles 22, as shown in FIG. 1. The pair of consumable receptacles 22 are defined by the lateral portions of the front screen 30 and generally are slots or openings sized to receive the consumables 24 to provide testing access (such as by sonorheometry) to one or more blood samples.

The central portion houses a display or other screen or device upon which the GUI is presented.

For example, the consumables 24 may include a cartridge or card 32 connected to a syringe 34. The card 32 includes an array of multiple chambers or wells 36 in a side-by-side or serial relationship that are accessible by the syringe 34 via an inlet and channels defined in the card 32 that distribute portions of the blood into the wells. Within each of the wells 36 is a blood sample dispensed by the syringe 34 and usually one or more reagents, such as is described in U.S. Prov. Pat. App. No. 61/443,088 filed on Feb. 15, 2011 and entitled, "Devices, Systems and Methods for Evaluation of Hemostasis," hereby incorporated in its entirety herein by reference. Different numbers of wells are possible, such as 2, 3 or 4 wells.

The term "blood sample" as used herein should be construed broadly to include such things as plasma or whole blood or some component of whole blood. For example, a blood sample may include blood, platelet poor plasma (PPP) or platelet rich plasma (PRP). If PPP or PRP are used for sonorheometry, however, ultrasound scattering material may be used in order to provide adequate ultrasound scattering to perform the measurements. For example, polystyrene beads can be used as they have neutral buoyancy in plasma.

Generally, when used herein the term "array" refers to spaced objects extending in a particular direction. The array configuration, however, could be any cluster or arrangement of the wells 36, not necessarily a linear one, wherein spacing along one axis is generally regular. Thus, the other axes could be somewhat offset from each other wherein the objects in the array extend in a common direction on one axis but are staggered above and below that axis. In the embodiment of FIG. 1, the wells 36 are in a serial array where they are not only regularly spaced, but in a straight line.

Disposed on one side of each of the wells 36 is a lens for coupling with and focusing sound or sonic energy emitted by corresponding sensors with operation supported by the electronics of the housing 20. This sonic energy is used to detect the mechanical parameters of the blood samples in the wells 36 which in turn are used to determine the hemostatic indexes using the principals described hereinabove.

In some embodiments of the present invention the GUI 16, includes a plurality of display portions 38 that are adjacent to and in a similar orientation to the sample wells 36. For example, the hemostatic indexes 12 may be depicted by an array of a similar number and orientation of graphical elements.

Each of the display portions 38 is configured to readily depict for easy interpretation, such as through numbers, colors or images, one of the hemostatic indexes 12. For example, the display portions 38 may include horizontal colored bars and percentage numbers that show parameters that include a coagulation factor function, a fibrinogen function (or concentration), a platelet function and/or a fibrinolysis function.

The colors of the colored bars may be used as a theme throughout the display and accompanying instructions and/or written documentation to associate information on a single one of the hemostatic indexes 12. For example, all items and documentation regarding the coagulation factor could be shown in red, the fibrinogen function in yellow, platelet function in purple and fibrinolytic function in light blue. In this manner, a healthcare person has a way to quickly associate various display items and documentation with the single function under stressful and fast-moving conditions.

The GUI 16 may also include a normal line 40 that when reached by the display portion visual indicator evidences a normal condition of the sample being tested.

Advantageously, the GUI is configured, through its display of the relative positioning of multiple (such as four) hemostatic indexes 12, to characterize hemostatic function and guide medical treatment. FIG. 3A, for example, shows a GUI from a hypothetical normal patient with no hemostatic defect. All of the hemostaic indexes 12 are at the same 100% (middle) level.

FIG. 3B shows a GUI from a hypothetical patient with reduced function of the coagulation factors (below 100%). This could be the consequence of anti-coagulation drugs, for example. Otherwise, in the case of a bleeding patient, fresh-frozen plasma can be administered to restore function of the coagulation factors.

FIG. 3C shows a GUI of a hypothetical patient with reduced platelet function, such as in the case of the patient receiving clopidogrel (Plavix®) or aspirin therapy. Otherwise, in the case of a bleeding patient, this readout indicates that platelet concentrates should be administered to restore platelet number and function to the patient.

FIG. 3D shows a GUI of a hypothetical patient with increased fibrinolytic function. In this case, a bleeding patient should be administered an anti-fibrinolytic drug such as aminocaproic acid or tranexamic acid.

FIG. 3E shows a GUI of a hypothetical patient with reduced function of both coagulation factors and platelets. The reduction in platelet function is more severe than that showed previously in FIG. 3C. In the case of a bleeding patient, the GUI of FIG. 3E indicates the need to transfuse fresh frozen plasma along with platelet concentrates.

FIG. 3F shows a GUI of a hypothetical patient with an increased function of the coagulation factors. The GUI is thus indicating a need for administration of anti-coagulant drugs such as coumadin, heparin, or direct thrombin inhibitors, for example, to restore normal function.

In another potential embodiment, the display of coagulation factors is divided into intrinsic and extrinsic coagulation factors to indicate defects that are specific to each activation pathway. The function of the intrinsic and extrinsic coagulation factors would be displayed along with the function of platelets, fibrinogen and fibrinolysis.

Figure 6:
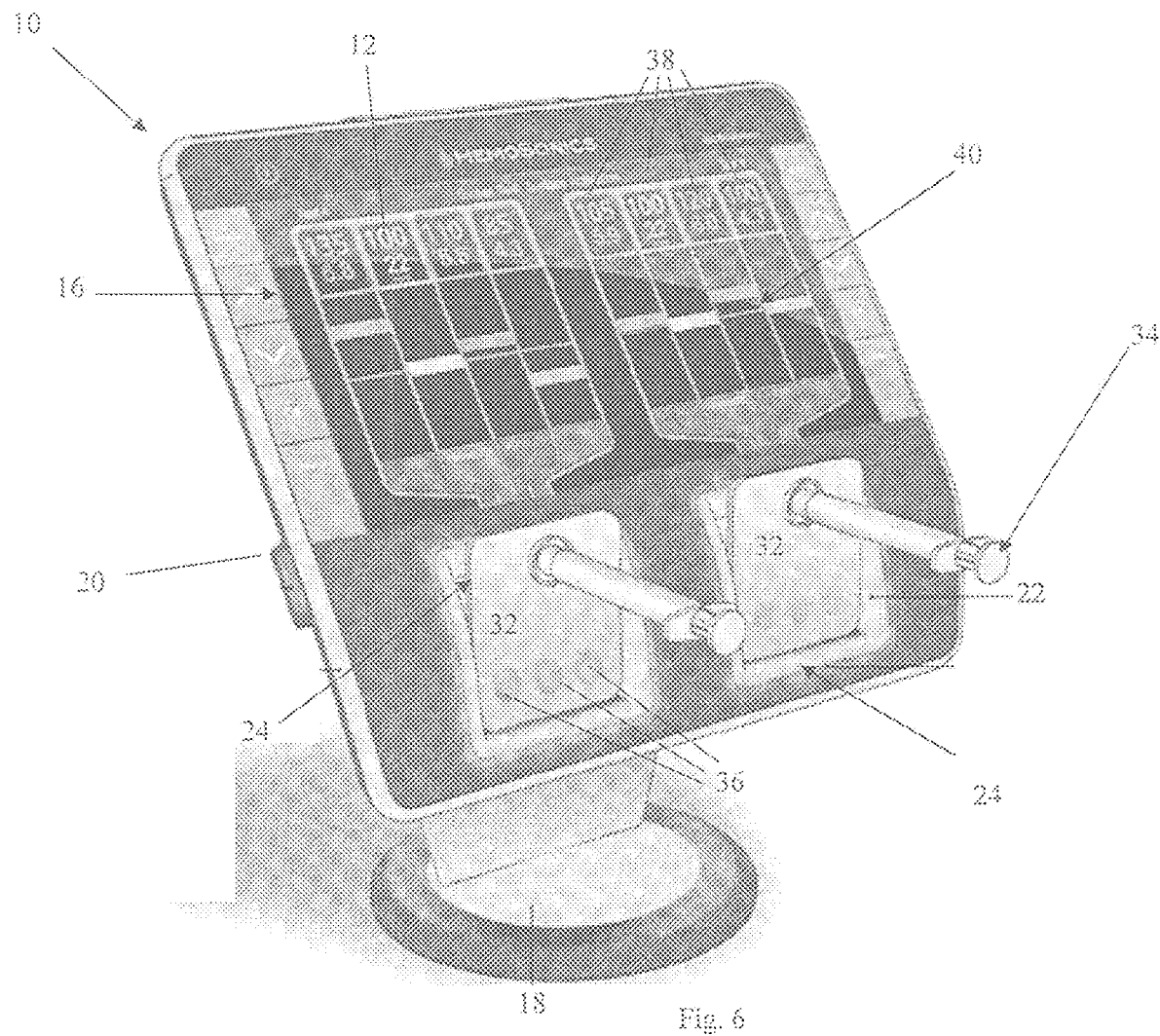
FIG. 6 is a perspective view of a functional hemostatic index determination and display system testing two subjects in parallel.
Figure 7:
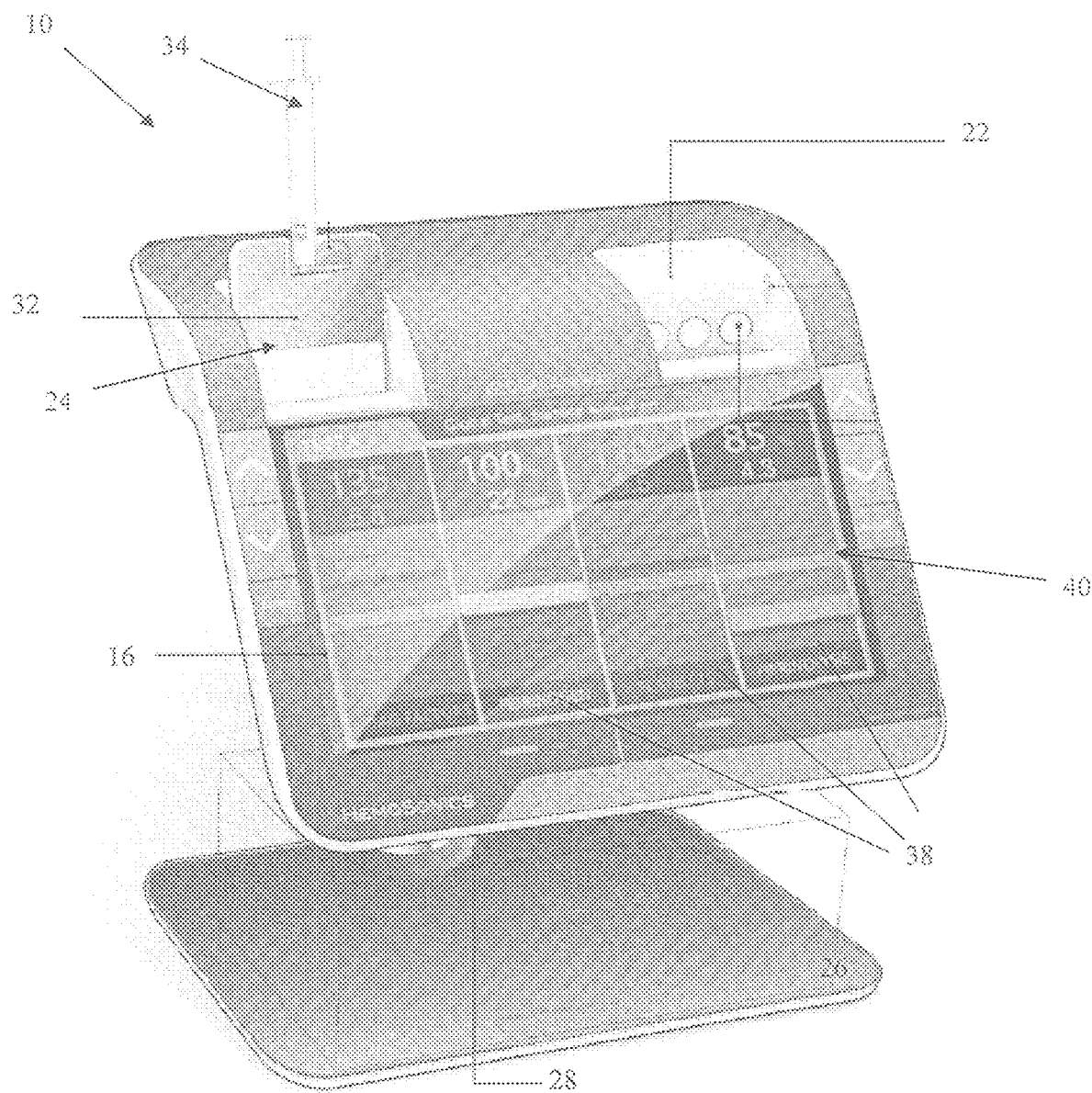
FIG. 7 is a perspective view of a functional hemostatic index determination and display system operating a surface activation test.

FIGS. 6 and 7 show other embodiments in which numerical scores are presented to quantify the function of the hemostatic components. Numerical scores can be presented as an arbitrary percentage or on an arbitrary numerical scale. In FIGS. 6 and 7, for example, the GUI displays 100% for normal physiological function. Also shown (except for fibrinogen) is display of an arbitrary scale going from 0 to 10 with 5.0 representing normal physiological function. Also, a light gray bar across the display represents the line 40 of normal physiological hemostasis.

Units of measure could also be used to quantify the absolute concentration or number of some of the output parameters. In FIGS. 6 and 7, functional fibrinogen concentration is quantified in units of mg/dl, for example.

The GUI 16 may also be configured to display the type of test administered to the blood samples. In FIG. 7, a Surface Activation Test is performed with the use of kaolin or celite, for example, to activate coagulation through the intrinsic (i.e., contact) activation pathway. Different types of tests and activations can be performed by selecting the appropriate reagent set which is detected by the system 10 from the pre-loaded consumables 24, such as through an RFID tag, and then communicated through the GUI 16.

FIG. 6 shows an embodiment simultaneously using two consumable receptacles 22 for parallel testing of blood samples. As in prior embodiments, the solid normal line 40 across the GUI 16 indicates normal physiological conditions.

Figure 8:
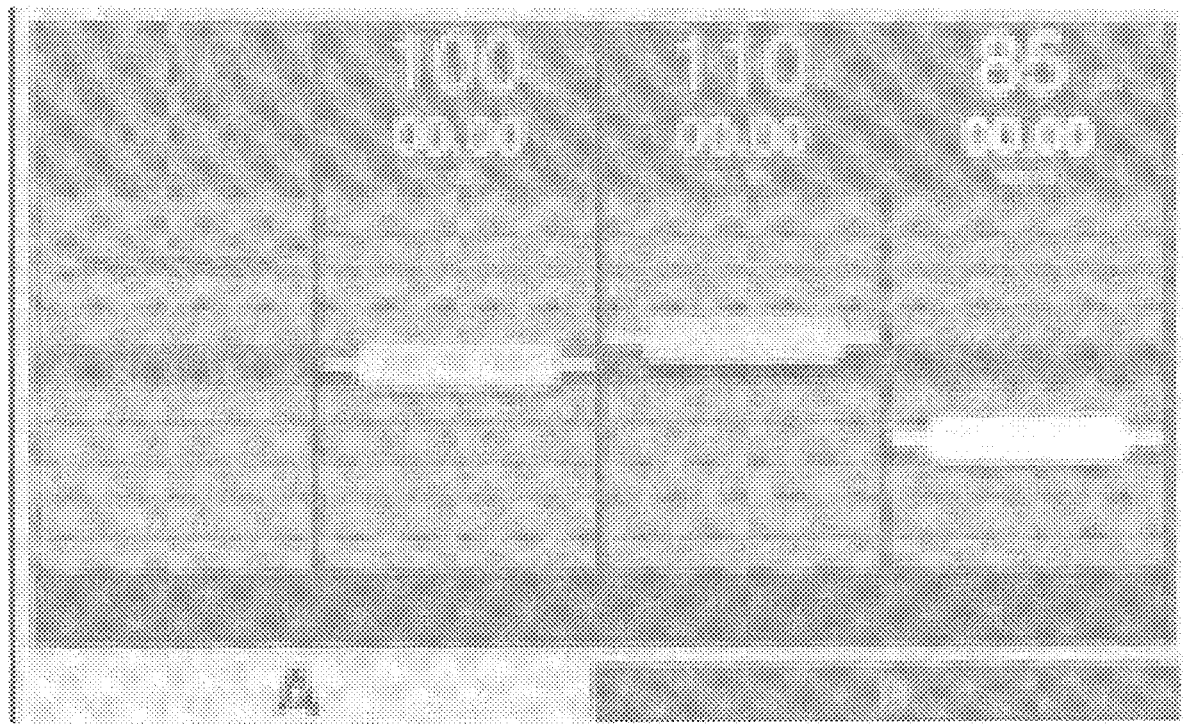
FIG. 8 is a GUI showing use of color to indicate normal and abnormal test results.

The GUI 16 may also be configured to dynamically change colors depending upon the status of the various hemostatic indexes 12. As shown in FIG. 8 for example, the graphical elements and numbers are color-coded with green representing normal, red representing increased function, and yellow representing reduced function.

In yet another embodiment, the GUI 16 may be configured to display additional hemostatic parameters such as: hematocrit (HCT), hemoglobin concentration (HGB) and/or red cell count (RBC). Display of the HCT, HGB or RBC values may inform the healthcare personnel to transfuse packed red blood cell units into a bleeding patient. Therefore, combining HCT, HGB, or RBC with the hemostatic indexes 12 can provide information about every possible transfusion product.

In other embodiments, the GUI 16 may be configured to display temporal progression of the hemostatic parameters. Such a display illustrates the progression of each hemostatic parameter as a function of procedure time, administered treatment (transfusions) and other landmark events.

Figure 4:
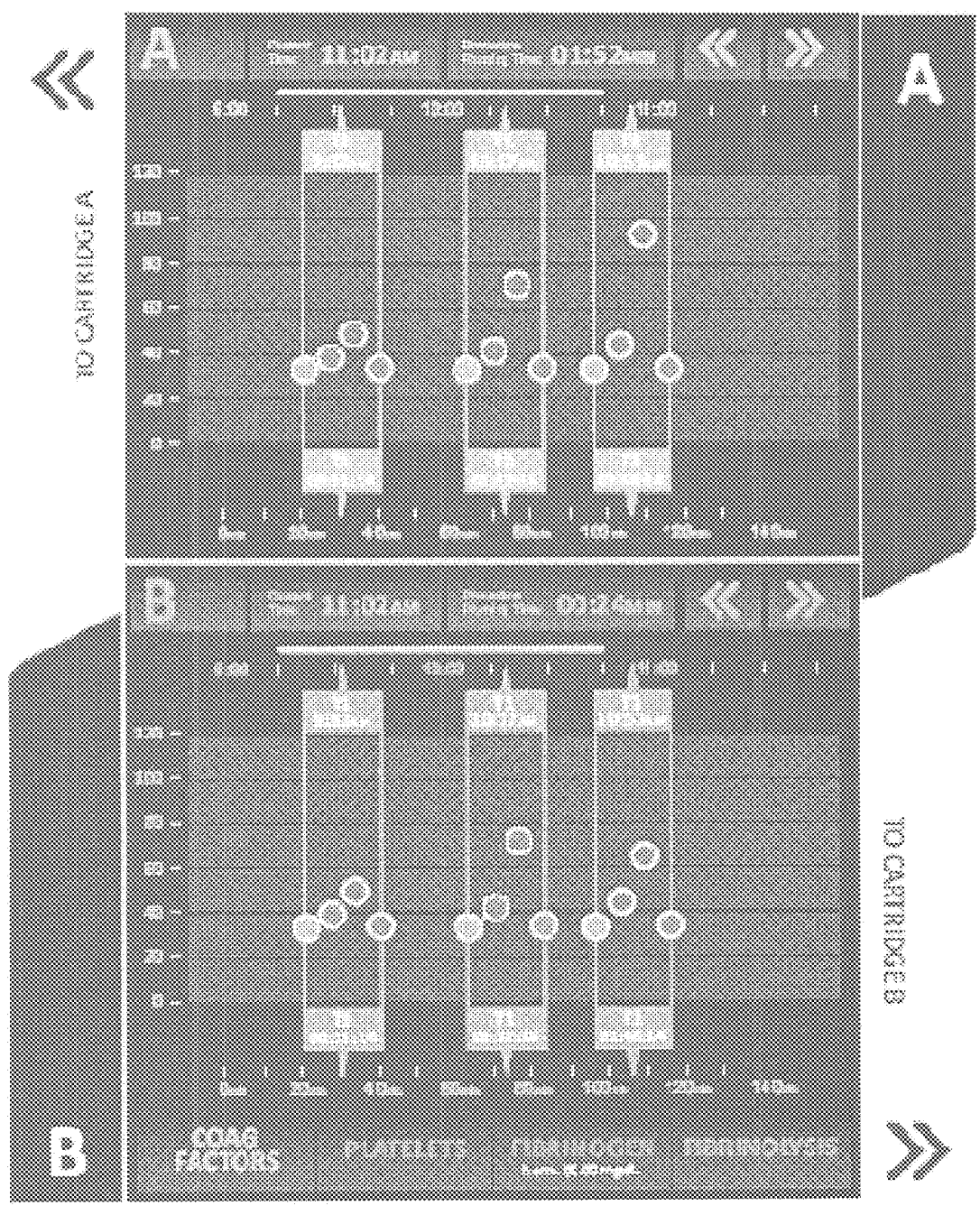
FIG. 4 shows a historical display of test results with multiple hemostatic indexes at various points in history.

FIG. 4, for example, shows three tests performed at three times (9:32 AM; 10:17 AM and 10:51 AM) during an hypothetical procedure in which both consumable receptacles (A and B) are used. Time relative to the beginning of the procedure is shown in the bottom scale, whereas absolute time is on the top scale. For each test performed there is an array of four color-coded symbols representing the four hemostatic indexes 12.

Figure 5:
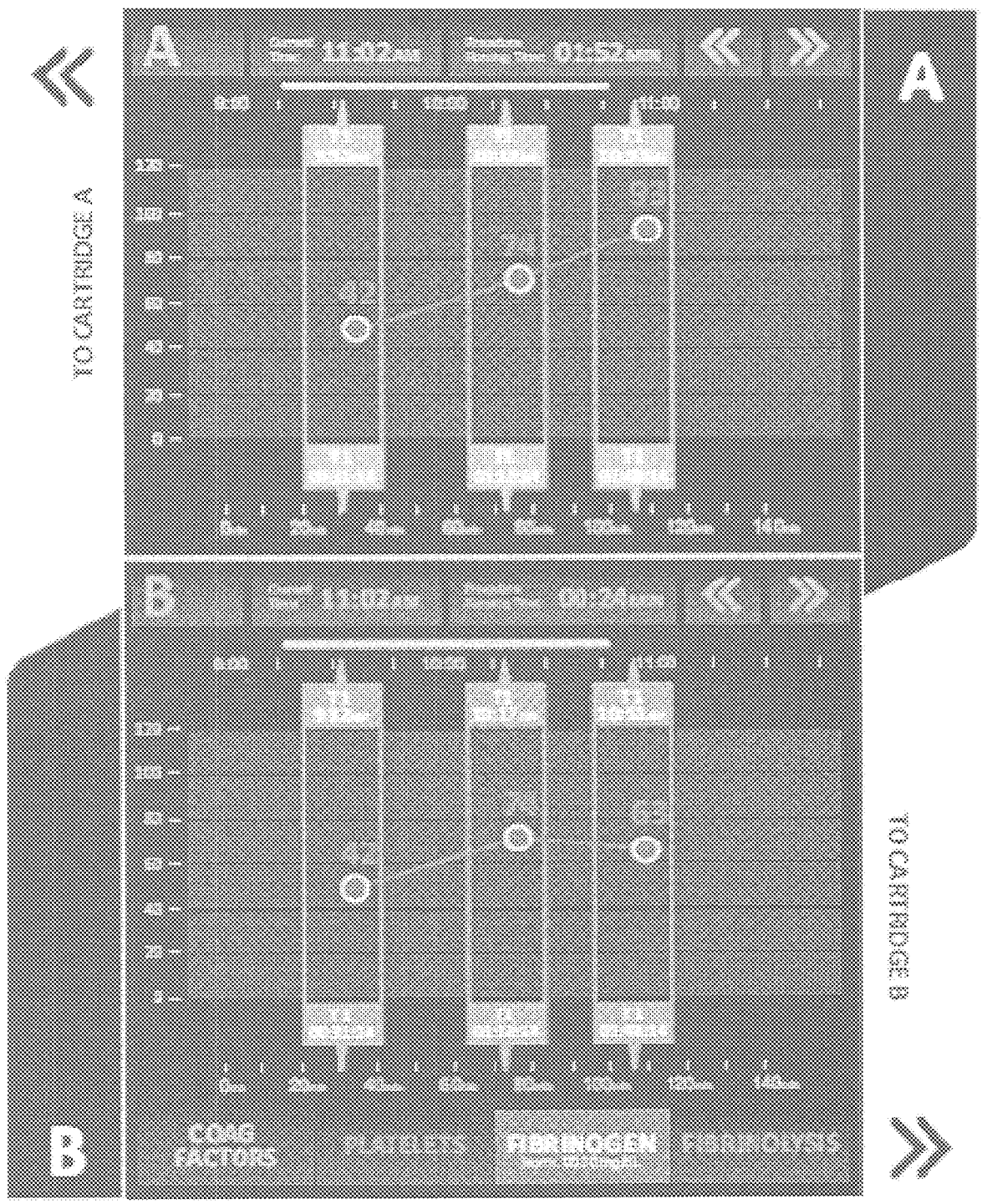
FIG. 5 shows a historical display with a single functional hemostatic index as it changes during the history.

FIG. 5 shows an embodiment wherein a single hemostatic parameter can be selected for temporal display by the GUI 16. In this case fibrinogen in mg/dL is shown as a function of procedure time.

Figure 9:
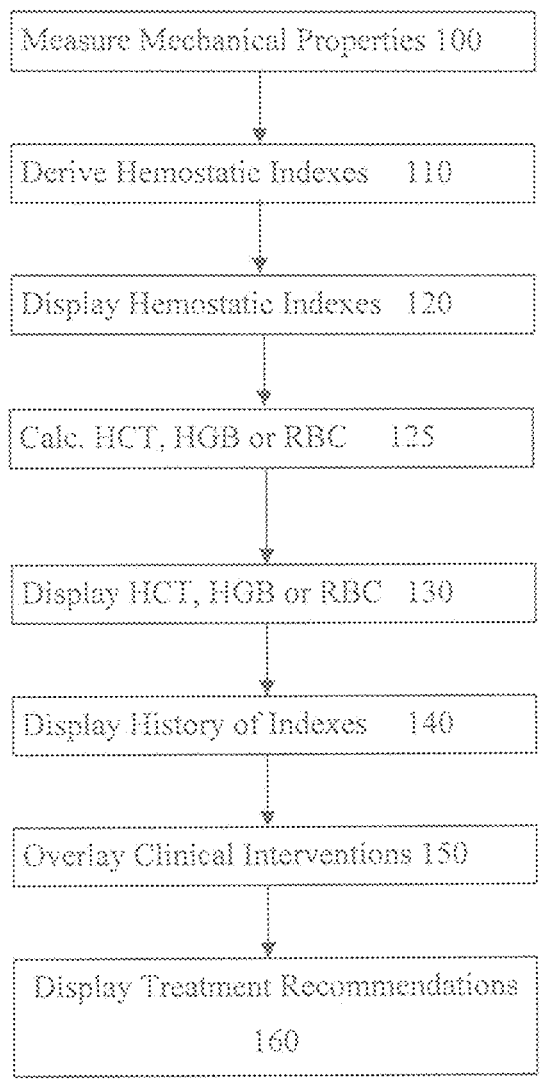
FIG. 9 is a method for determining and displaying a plurality of hemostatic indexes.

In another embodiment, as shown in FIG. 9, the present invention includes a method for deriving and displaying hemostatic indexes. Mechanical properties of blood samples are measured 100 to generate independent measurements. The hemostatic indexes are derived 110 from the independent measurements. For example, one or more of a coagulation factor function, a fibrinogen concentration, a fibrinogen function, a platelet function and a fibrinolysis function may be derived in step 110. Also derived 110 from the independent measurements may be a hematocrit, hemoglobin concentration and/or red cell count.

Deriving 110 may also include deriving each of the hemostatic indexes from a plurality of the independent measurements. Also, deriving 110 may include deriving each of the hemostatic indexes from a corresponding one of the independent measurements.

The method may also include displaying 120 the hemostatic indexes, such as by using the GUI 16. For example, displaying 120 may include displaying a numerical score and/or a graphical element for the hemostatic indexes. Also, displaying 120 may include displaying a changing color to indicate dynamic changes in the hemostatic indexes or a same color to associate the hemostatic indexes with other information.

The method may also include estimating or calculating 125 and displaying 130 hematocrit, hemoglobin concentration and/or red cell count simultaneously with the at least two hemostatic indexes.

The method may also include displaying 140 a history of the hemostatic indexes and overlaying 150 one or more clinical interventions on the history. For example, displaying 140 the history may include displaying an array of graphical indicators each representing one of the hemostatic indexes at some time in the history. The graphical indicators may be positioned relative to each other to communicate a hemostatic condition of a subject at that point in time.

The method may also include displaying 160 a treatment recommendation based on the at least two hemostatic indexes. For example, the GUI 16 could display information guiding transfusion of at least one of platelets, cryoprecipitate, plasma, red cells or antifibrinolytics, or guiding therapies using an anti-platelet drug, anti-coagulant drug or pro-fibrinolysis drug.

In another embodiment, the system 10 is configured to determine a range of possible values given the current results of the measurements of the blood sample. In this manner, the healthcare personnel may receive early indication of trend without having to wait the fully elapsed time. For example, as shown by the progression from FIGS. 10-18, determination of coagulation factor function becomes progressively more confident as indicated by the vertical bar displayed by the GUI 16 on the right and the associated numerical information.

Figure 10:
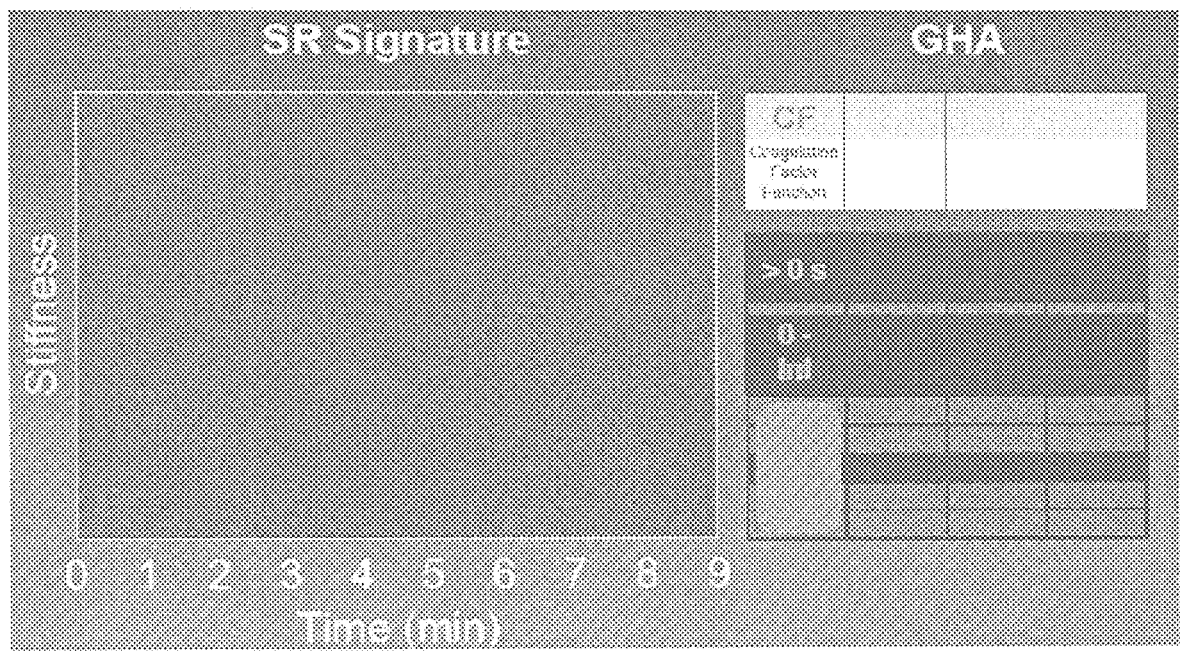
FIGS. 10-18 show a graphical display of a graphical element (a bar) that dynamically shrinks as measurement confidence increases during determination of a functional hemostatic index.
Figure 11:
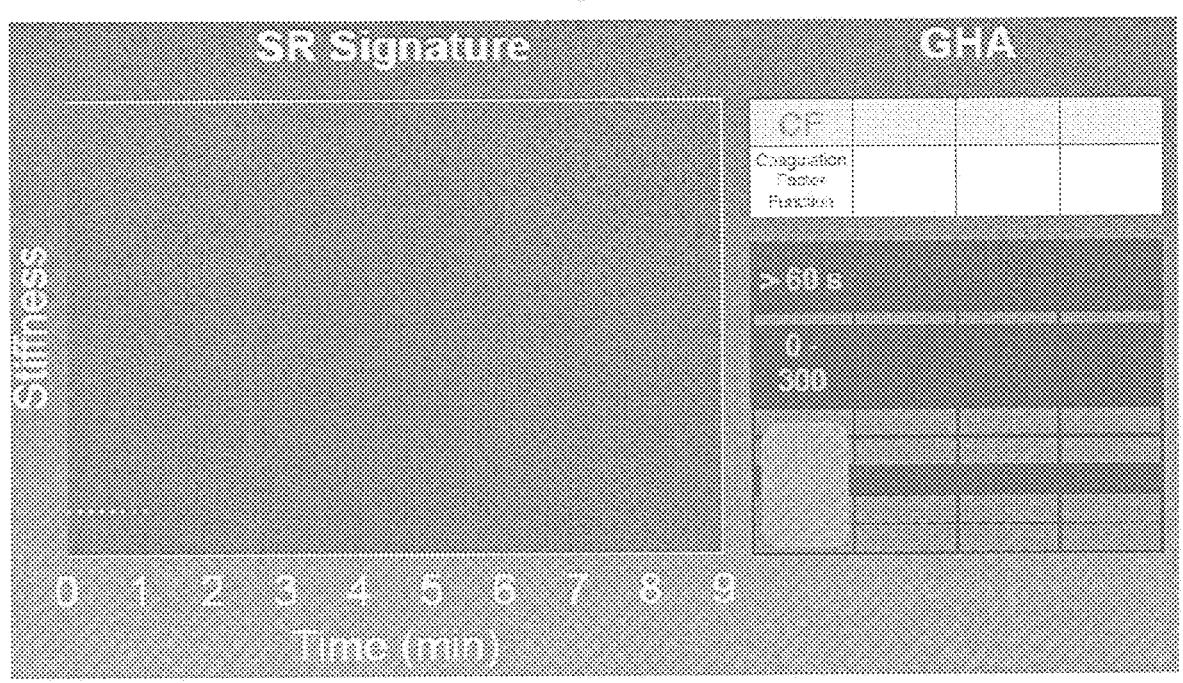
Figure 12:
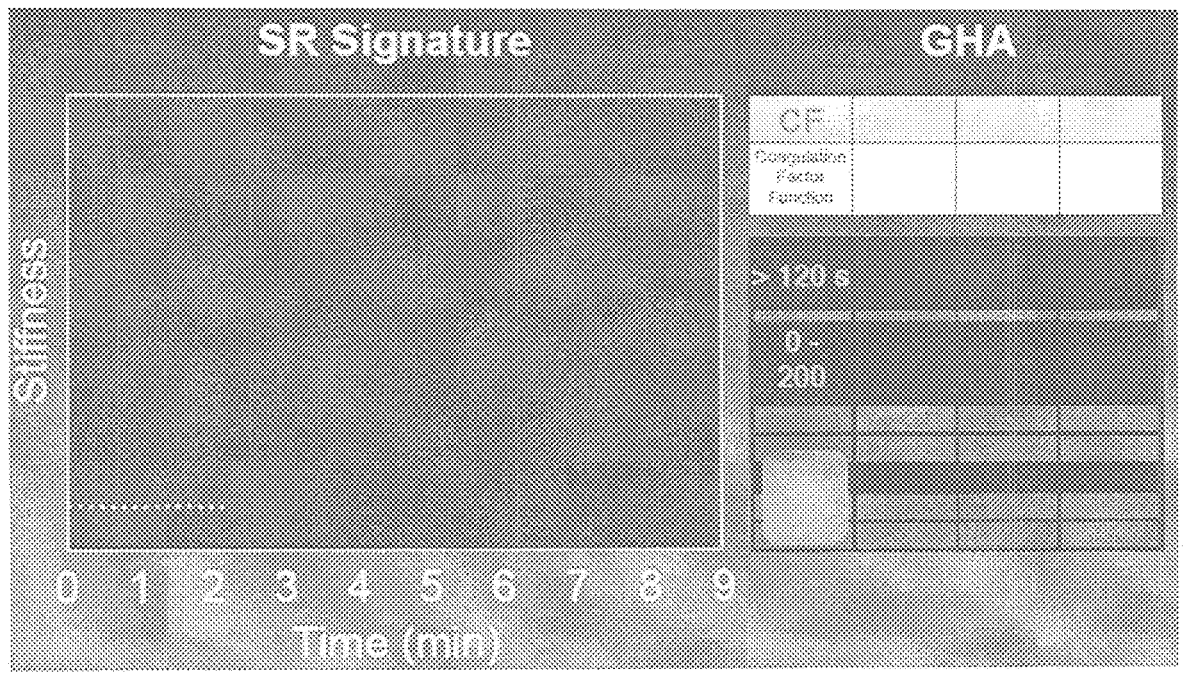
Figure 13:
Figure 14:
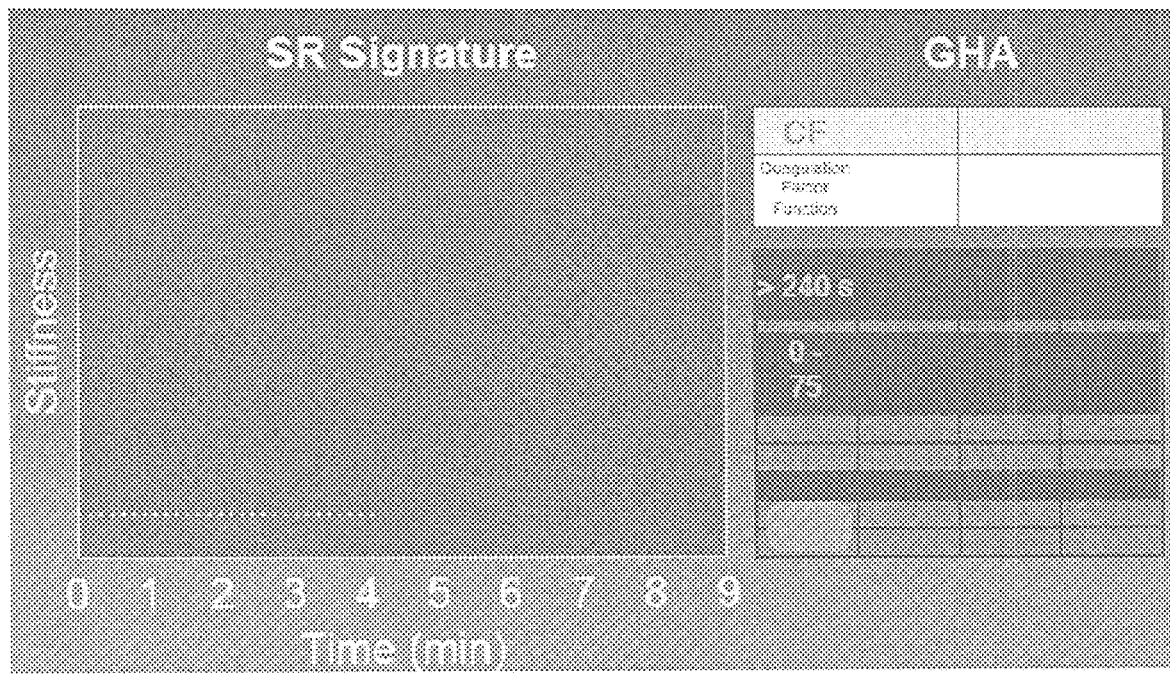
Figure 15:
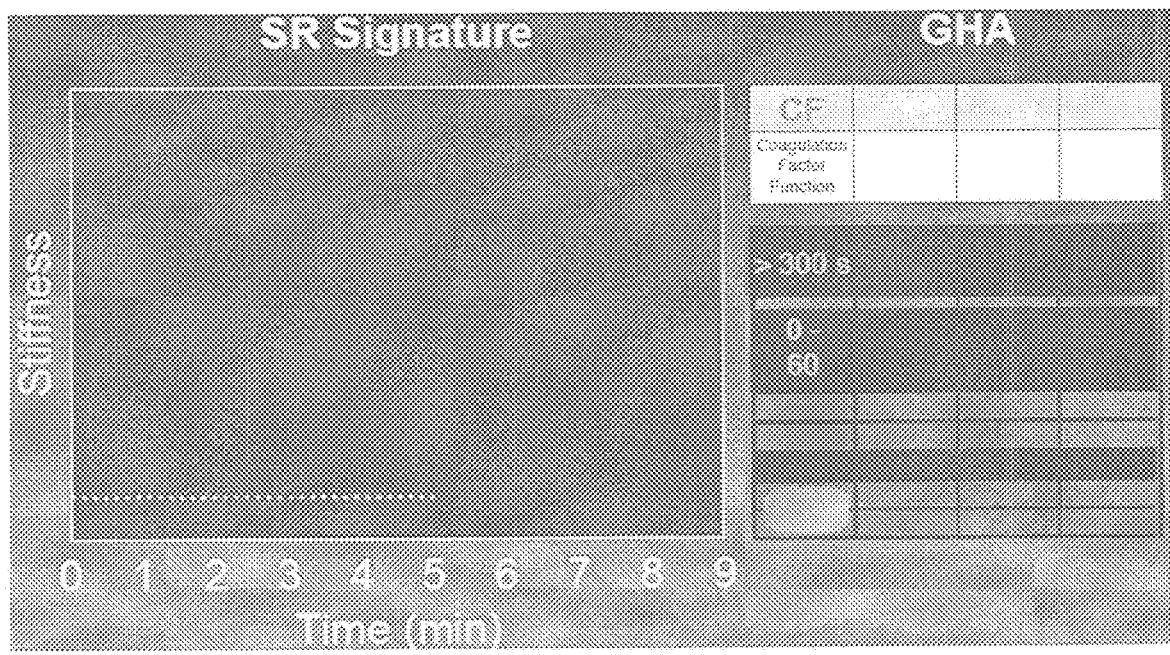
Figure 16:
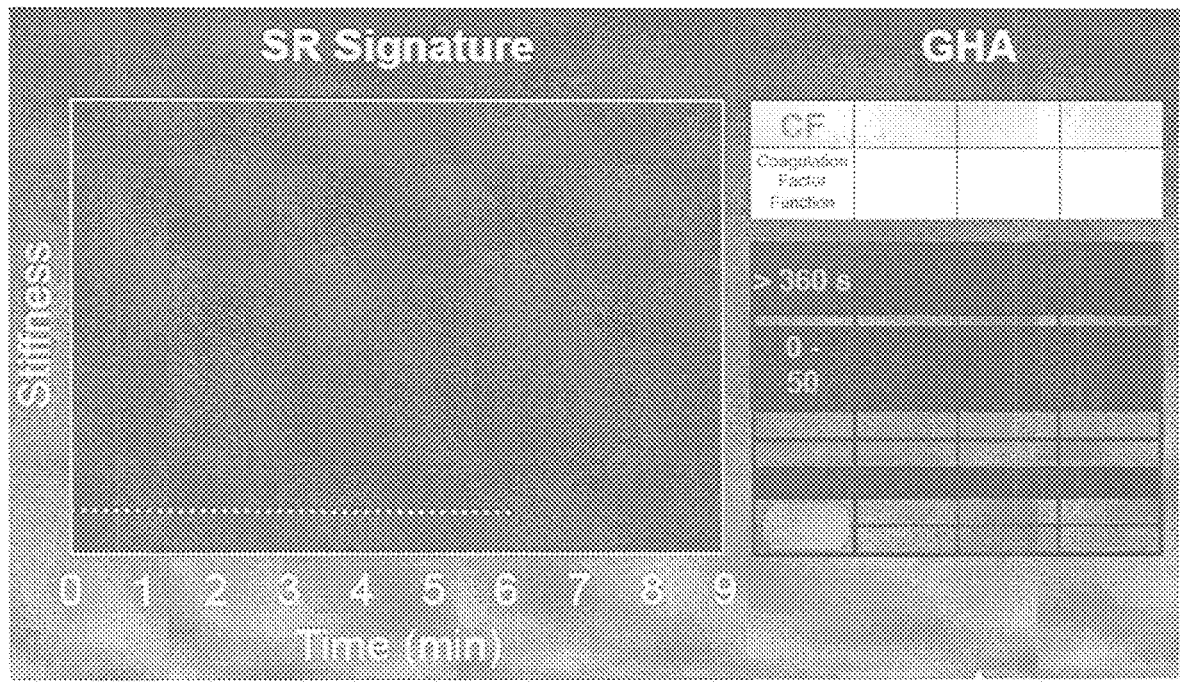
Figure 17:
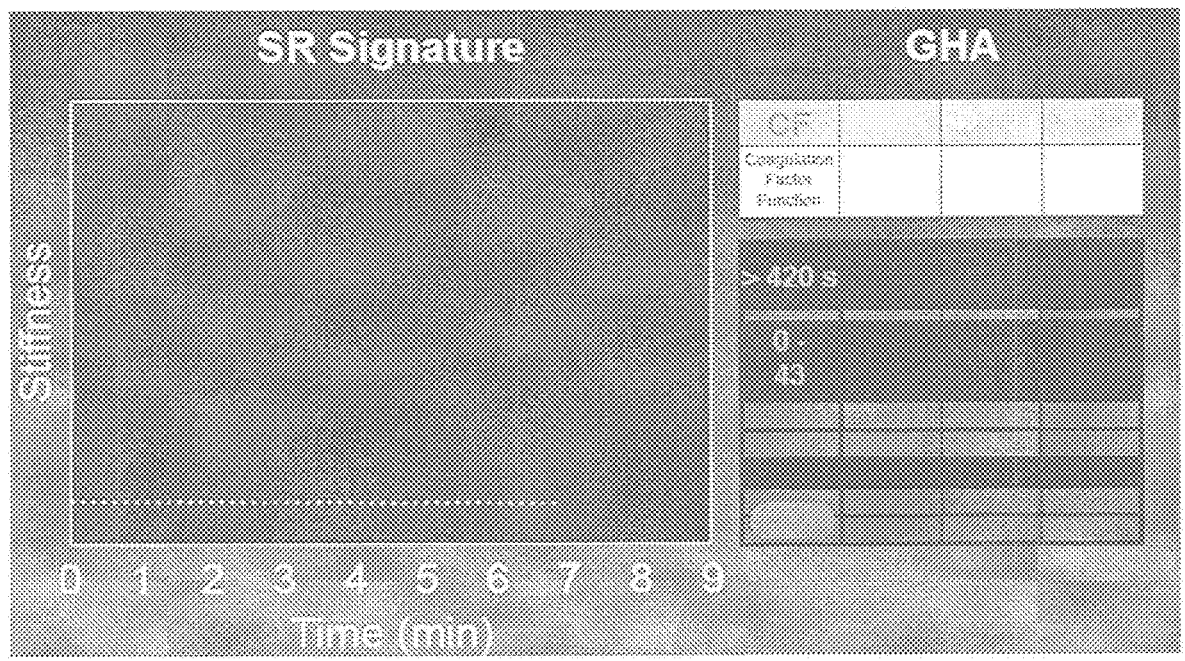
Figure 18:
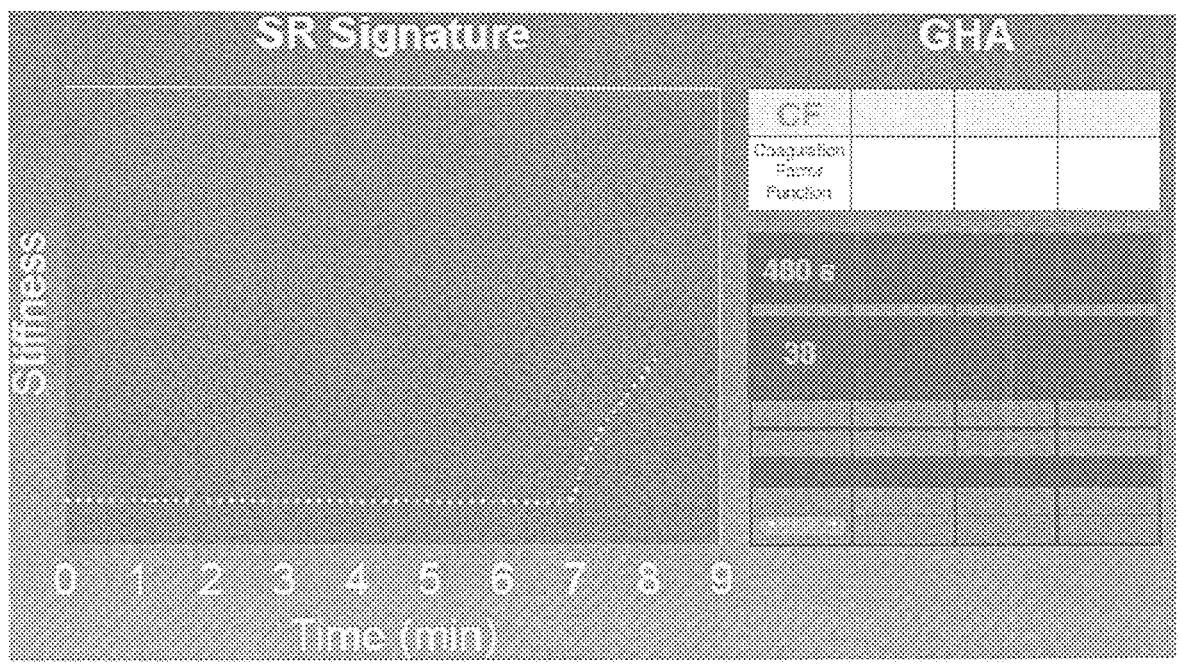

Each of the figures is a 60 second interval, starting with time zero in FIG. 10 wherein a zero to infinite range of the possible 100% normalized index is shown. As each time interval passes, the range and accompanying height of the bar shrinks to express increasing certainty around the projected result. At 1 minute the range is 0-300; at 2 minutes 0-200; at 3 minutes 0-100 (since normal is 3.5 minutes+/−10% CF will definitely not be high with no change in the stiffness); at 4 minutes 0-75 (now the patient must be in low territory because they're outside the normal range at the 3.85 minute high end); at 5 minutes the range drops to 0-60; at 6 minutes 0-50; at 7 minutes 0-43 and with the final result at 8 minutes of 38.

Notably, the GUI 16 is configured to continuously shrink the height of the bar (or other visual characteristic) to show increasing confidence with the final minimum thickness and a white line indicating the final result.

Figure 19:
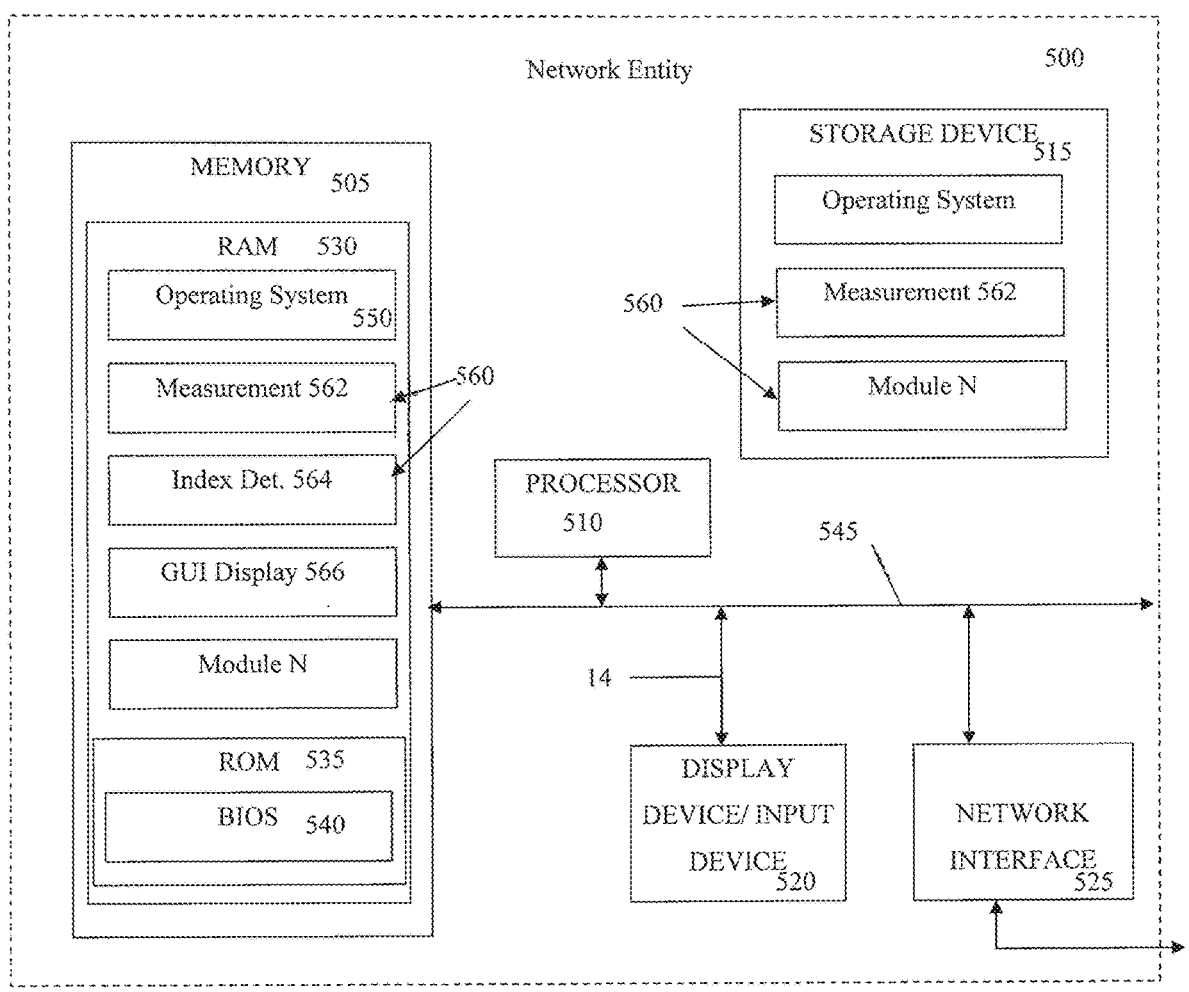
FIG. 19 is a schematic of a functional hemostatic index determination and display system as a network entity.

Referring now to FIG. 19, a schematic diagram of a central server 500, or similar network entity, configured to implement a VPD system, according to one embodiment of the invention, is provided. As used herein, the designation "central" merely serves to describe the common functionality the server provides for multiple clients or other computing devices and does not require or infer any centralized positioning of the server relative to other computing devices.

As may be understood from FIG. 19, in this embodiment, the central server 500 may include a processor 510 that communicates with other elements within the central server 500 via a system interface or bus 545. Also included in the central server 500 may be a display device/input device 520 for receiving and displaying data, such as via the GUI 16 described above. This display device/input device 520 may be, for example, a keyboard or pointing device that is used in combination with a monitor. The central server 500 may further include memory 505, which may include both read only memory (ROM) 535 and random access memory (RAM) 530. The server's ROM 535 may be used to store a basic input/output system 540 (BIOS), containing the basic routines that help to transfer information across the one or more networks.

In addition, the central server 500 may include at least one storage device 515, such as a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the art, each of these storage devices 515 may be connected to the system bus 545 by an appropriate interface. The storage devices 515 and their associated computer-readable media may provide nonvolatile storage for a central server. It is important to note that the computer-readable media described above could be replaced by any other type of computer-readable media known in the art. Such media include, for example, magnetic cassettes, flash memory cards and digital video disks.

A number of program modules may be stored by the various storage devices and within RAM 530. Such program modules may include an operating system 550 and a plurality of one or more (N) modules 560. The modules 560 may control certain aspects of the operation of the central server 500, with the assistance of the processor 510 and the operating system 550. For example, the modules may include a measurement module 562 for measuring mechanical properties of a blood sample, a hemostatic index determination module 564 and a display module 566.

The flowchart and block diagrams, such as in FIGS. 9 and 19, illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A system for measuring physiologic parameters of a single blood sample, the system comprising:
   a receptacle to receive a cartridge, the cartridge having:
      a plurality of sample wells including a first sample well and a second sample well; and
      a plurality of channels including i) a first channel connected in fluid communication to the first sample well and ii) a second channel connected in fluid communication to the second sample well;
      wherein the plurality of channels have a collective connection configured to establish fluid communication with the single blood sample for drawing, from the single blood sample, portions for each of the first and second the sample wells including a first portion for the first sample well and a second portion for the second sample well, respectively;
   a sensor system configured to couple with the receptacle for interrogation of the plurality of portions of the single blood sample including the first and second portions of the single blood sample to yield a plurality of sets of independent measurements including a first set of independent viscoelastic measurements from the first portion and a second set of independent viscoelastic measurements from the second portion;
   a processor connected to the sensor system to continually receive the plurality of sets of independent measurements, including a data sets associated with the first set of independent viscoelastic measurements and a data sets associated with the second set of independent viscoelastic measurements, the processor being configured, via a set of instructions stored in memory, to estimate physiologic parameters of the single blood sample; and
   a graphical user interface (GUI) connected to the processor and configured to simultaneously display functional hemostatic index derived from each of the plurality of independent measurements, wherein each displayed functional hemostatic index of the simultaneously displayed functional hemostatic indexes comprise a coagulation factor function, a fibrinogen function, and the platelet function, wherein the graphical user interface comprises a graphical indicator for each of the displayed hemostatic indexes.

2. The system of claim 1, wherein the sensor system comprises mechanical transducers.

3. The system of claim 1, wherein the sensor system comprises ultrasonic transducers.

4. The system of claim 1, wherein the coagulation factor function includes an intrinsic activation factor.

5. The system of claim 1, wherein the coagulation factor function includes an extrinsic activation factor.

6. The system of claim 1, wherein graphical indicator includes i) a numerical output and a corresponding visual element that quantifies a function of the each of the simultaneously displayed functional hemostatic indexes and ii) relative positioning of the each of the simultaneously displayed functional hemostatic indexes to communicate a hemostatic condition of a subject, and wherein the relative positioning shows a range associated with normal physiological function.

7. The system of claim 1, wherein the displayed functional hemostasis indexes further include a fibrinogen concentration.

8. The system of claim 1, wherein the displayed functional hemostasis indexes further include a fibrinolysis function.

9. The system of claim 1, wherein the GUI is further configured to display a parameter selected from the group consisting of a hematocrit, hemoglobin concentration and red cell count.

10. The system of claim 9, wherein the GUI is further configured to display the parameter selected from the group consisting of the hematocrit, hemoglobin concentration and red cell count simultaneously with the simultaneously displayed functional hemostatic indexes.

11. The system of claim 1, wherein the receptacle is configured to be consumable and is configured to position the first and second portions of the single blood sample of the first and second sample wells, respectively, in a spatial arrangement corresponding to the simultaneously displayed functional hemostatic indexes.

12. The system of claim 1, wherein the GUI is configured to display the functional hemostatic indexes in a side-by-side serial arrangement corresponding to a spatial arrangement associated with the sample wells.

13. The system of claim 1, wherein the GUI is further configured to display a history of the simultaneously displayed functional hemostatic indexes.

14. The system of claim 13, wherein at least one portion of the history includes an array of graphical indicators, each of the graphical indicators representing one of the simultaneously displayed functional hemostatic indexes at some time in the history.

15. The system of claim 1, wherein each of the graphical indicators includes the relative positioning that shows a range associated with abnormal physiological function for the each of the simultaneously displayed functional hemostatic indexes.

16. The system of claim 1, wherein the GUI is further configured to display a treatment recommendation based on the simultaneously displayed functional hemostatic indexes.

17. The system of claim 16, wherein the treatment recommendation is for guiding transfusion of a blood component selected from the group consisting of platelets, cryoprecipitate, fibrinogen, plasma, red cells, and antifibrinolytics.

18. The system of claim 17, wherein the treatment recommendation is for guiding therapies of a drug selected from the group consisting an anti-platelet drug, an anticoagulant drug, and a pro-fibrinolysis drug.

19. The system of claim 1, wherein during the interrogation of the portions of the single blood sample i) the first sample well comprises the first portion of the single blood sample mixed with a first reagent or a first combination of reagents configured to activate coagulation and ii) the second sample well comprises the second portion of the single blood sample mixed with a second combination of reagents that includes a) a reagent, or a combination of reagents, configured to activate coagulation and b) a reagent, or a combination of reagents, configured to inhibit platelet aggregation.

20. The system of claim 1, wherein during the interrogation of the portions of the single blood sample i) the first sample well comprises the first portion of the single blood sample mixed with a first reagent or a first combination of reagents configured to activate coagulation and ii) the second sample well comprises the second portion of the single blood sample mixed with a second combination of reagents that includes a) a reagent, or a combination of reagents, configured to activate coagulation and b) a reagent, or a combination of reagents, configured to inhibit platelet aggregation.

21. A method for measuring physiologic parameters of a single blood sample, the method comprising:
   interrogating a cartridge to provide a plurality of sets of independent measurements including a first set of independent viscoelastic measurements from the first portion and a second set of independent viscoelastic measurements from the second portion; wherein the cartridge has (i) a plurality of sample wells including a first sample well and a second sample well and (ii) a plurality of channels including a) a first channel connected in fluid communication to the first sample well and b) a second channel connected in fluid communication to the second sample well, wherein the plurality of channels have a collective connection configured to establish fluid communication with the single blood sample for drawing, from the single blood sample, portions for each of the first and second the sample wells including a first portion for the first sample well and a second portion for the second sample well, respectively;
   continually receiving, by a processor, the plurality of sets of independent measurements, including a data sets associated with the first set of independent viscoelastic measurements and a data sets associated with the second set of independent viscoelastic measurements;
   estimating, by the processor, a functional hemostatic index associated with the platelet function by differentially combining results derived from at least the first and second independent measurements; and
   simultaneously displaying, via a graphical user interface, functional hemostatic indexes derived from each of the plurality of independent measurements, wherein each displayed functional hemostatic index of the simultaneously displayed functional hemostatic indexes comprise a coagulation factor function, a fibrinogen function, and the platelet function, and wherein the graphical user interface comprises a graphical indicator for each of the displayed hemostatic indexes.

* * * * *